(12) United States Patent
Guyon et al.

(10) Patent No.: US 11,738,182 B2
(45) Date of Patent: *Aug. 29, 2023

(54) REINFORCED BALLOON CATHETER

(71) Applicant: MicroVention, Inc., Aliso Viejo, CA (US)

(72) Inventors: Roland Guyon, Cowan Heights, CA (US); Nelson Peralta, Rancho Santa Margarita, CA (US); Raleigh Purtzer, San Clemente, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 308 days.

This patent is subject to a terminal disclaimer.

(21) Appl. No.: 16/940,205

(22) Filed: Jul. 27, 2020

(65) Prior Publication Data

US 2020/0353230 A1 Nov. 12, 2020

Related U.S. Application Data

(63) Continuation of application No. 15/605,820, filed on May 25, 2017, now Pat. No. 10,786,659.

(60) Provisional application No. 62/380,979, filed on Aug. 29, 2016, provisional application No. 62/344,371, filed on Jun. 1, 2016.

(51) Int. Cl.
*A61M 25/10* (2013.01)
*A61M 25/00* (2006.01)
*A61M 25/01* (2006.01)

(52) U.S. Cl.
CPC .. *A61M 25/10187* (2013.11); *A61M 25/0052* (2013.01); *A61M 25/0108* (2013.01); *A61M 25/1006* (2013.01); *A61M 25/0045* (2013.01); *A61M 25/1034* (2013.01); *A61M 25/10182* (2013.11); *A61M 2025/0018* (2013.01); *A61M 2025/1077* (2013.01); *A61M 2025/1079* (2013.01)

(58) Field of Classification Search
CPC ........ A61M 25/10187; A61M 25/0052; A61M 25/0108; A61M 25/1006; A61M 25/0045; A61M 25/10182; A61M 25/1034; A61M 2025/1077; A61M 2025/1079
See application file for complete search history.

(56) References Cited

U.S. PATENT DOCUMENTS

| 4,692,220 | A | | 9/1987 | Auel et al. |
| 4,821,722 | A | * | 4/1989 | Miller ................ A61M 29/02 |
| | | | | 606/192 |

(Continued)

FOREIGN PATENT DOCUMENTS

| EP | 0284672 A1 | 10/1988 |
| EP | 0515332 A1 | 11/1992 |
| EP | 2853211 A1 | 4/2015 |

OTHER PUBLICATIONS

European Patent Office, Supplementary European Search Report dated Jan. 20, 2020 in European Patent Application No. 17807274, 5pp.

(Continued)

*Primary Examiner* — Phong Son H Dang
(74) *Attorney, Agent, or Firm* — Inskeep IP Group, Inc.

(57) ABSTRACT

A balloon catheter is described having a reinforced, co-axial, duel lumen design. In some embodiments, the balloon catheter includes a purging mechanism designed to purge air from the balloon.

18 Claims, 19 Drawing Sheets

(56) References Cited

U.S. PATENT DOCUMENTS

| | | | |
|---|---|---|---|
| 5,100,385 A * | 3/1992 | Bromander | A61M 25/104 604/99.03 |
| 5,135,486 A * | 8/1992 | Eberle | A61M 25/104 604/103.1 |
| 5,372,138 A | 12/1994 | Crowley et al. | |
| 5,599,301 A | 2/1997 | Jacobs et al. | |
| 6,102,931 A | 8/2000 | Thornton | |
| 6,994,687 B1 | 2/2006 | Shkolnik | |
| 7,070,606 B2 | 7/2006 | Seward | |
| 7,160,266 B2 | 1/2007 | Shkolnik | |
| 7,641,531 B2 | 1/2010 | Yamazaki | |
| 7,641,631 B2 * | 1/2010 | Chin | A61M 25/0075 604/96.01 |
| 8,177,806 B2 | 5/2012 | Chin et al. | |
| 2003/0212360 A1 * | 11/2003 | Shkolnik | A61M 25/104 604/103 |
| 2009/0076439 A1 | 3/2009 | Dollar et al. | |
| 2012/0245521 A1 * | 9/2012 | Gulachenski | A61M 25/1036 604/103.09 |
| 2014/0031746 A1 | 1/2014 | Yanuma | |
| 2014/0188043 A1 * | 7/2014 | Shibahara | A61M 25/1006 604/96.01 |

OTHER PUBLICATIONS

WIPO, U.S. International Search Authority, International Search Report and Written Opinion dated Aug. 24, 2017 in International Patent Application No. PCT/US2017/034571, 9 pages.

Japanese Patent Office, Office Action dated Jul. 7, 2020 with English translation in Japanese Patent Application No. JP 2018-563477, 6 pages.

* cited by examiner

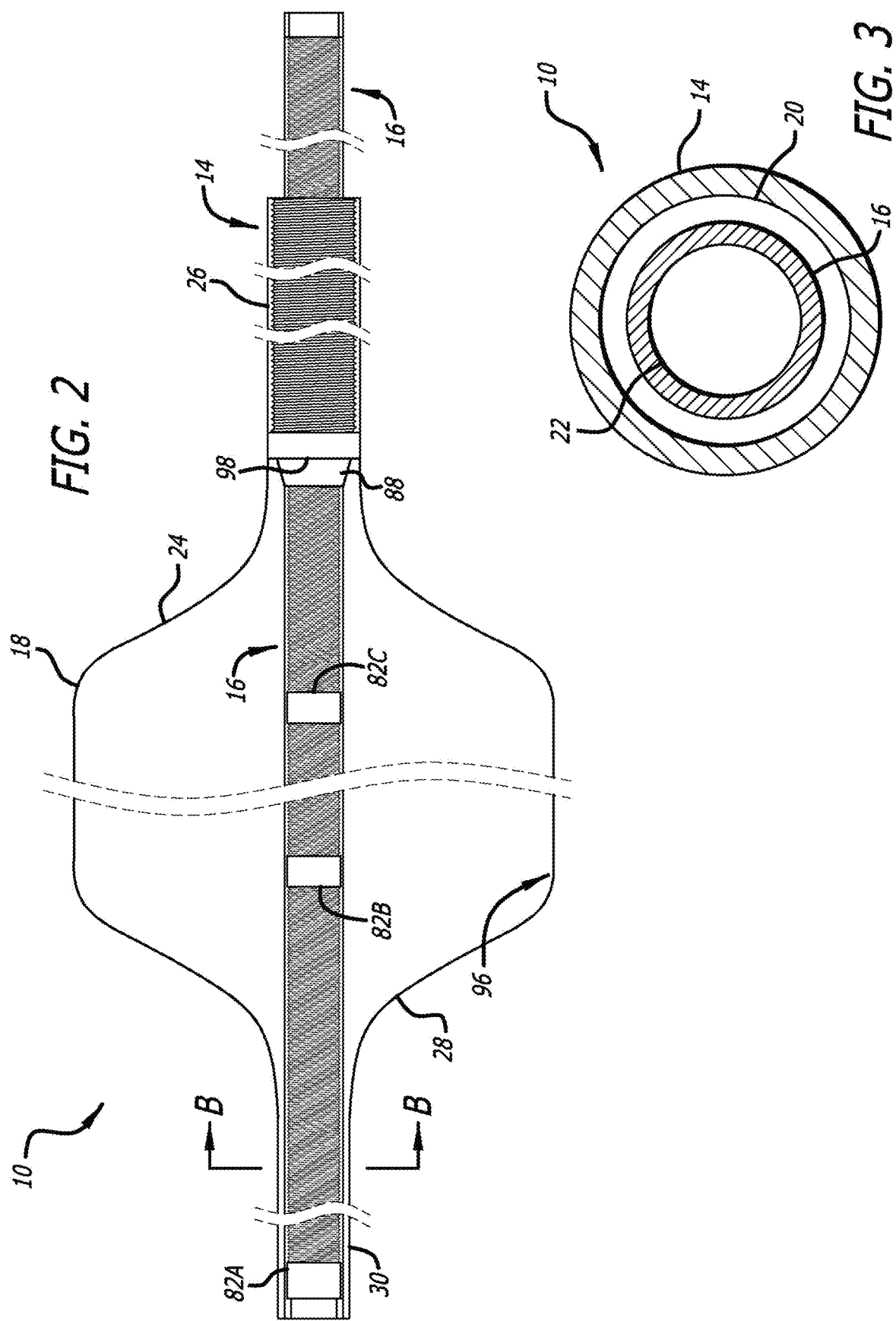

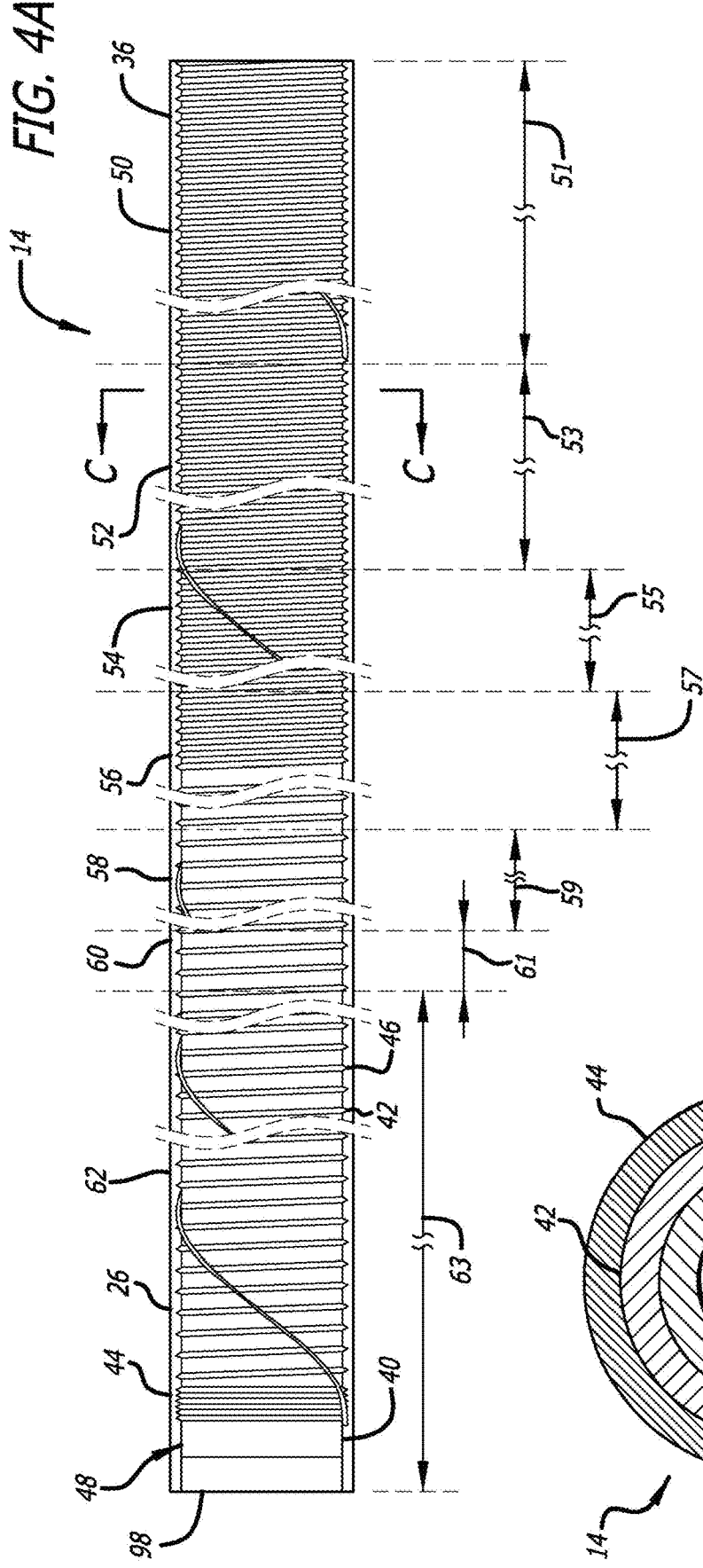

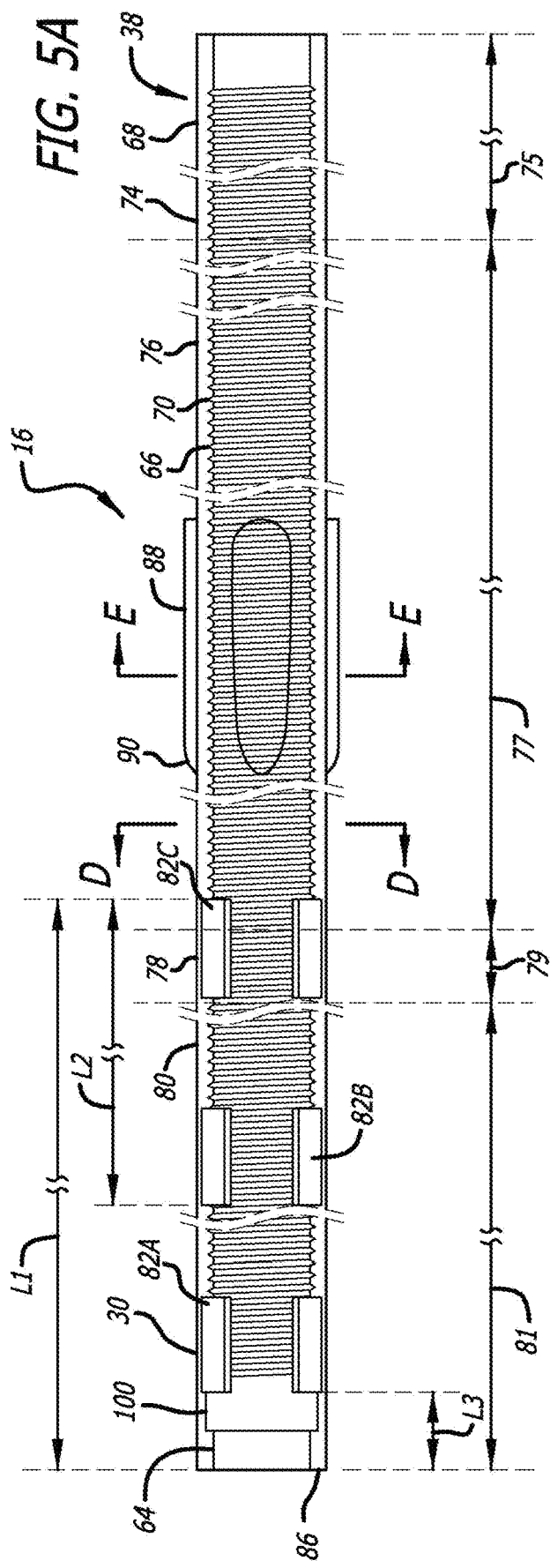

REINFORCED BALLOON CATHETER

RELATED APPLICATIONS

This application is a continuation of and claims priority to U.S. patent application Ser. No. 15/605,820 filed May 25, 2017 entitled Improved Reinforced Balloon Catheter, which claims benefit of and priority to U.S. Provisional Application Ser. No. 62/344,371 filed Jun. 1, 2016, entitled Reinforced Balloon Catheter, and to U.S. Provisional Application Ser. No. 62/380,979 filed Aug. 29, 2016, entitled Porosity Purging System for Catheter, all of which are hereby incorporated herein by reference in their entireties.

FIELD OF THE INVENTION

The present invention relates to balloon catheters and, more particularly, to balloon catheters for use in neurological procedures.

BACKGROUND OF THE INVENTION

Balloon catheters are increasingly being employed to conduct neurological procedures in patients. However, the design parameters for balloon catheters intended for use in neurological procedures are significantly different than the design parameters for balloon catheters used in non-neurological procedures such as cardiological procedures. For example, the width of the circulatory system within the neuroanatomy is significantly smaller and more tortuous than the circulatory system in other parts of the body. In order to access the smaller and more tortuous regions of the neuroanatomy, it is necessary to minimize the outer diameter of the balloon catheter while simultaneously maintaining the pushability and trackability of the catheter.

Balloon catheters and balloons for neurovasculature use offer particular design complications given the small design profile. Balloon catheters often utilize a purging system to purge residual air from the balloon catheter prior to placement in the vasculature. However, purging systems still may leave an escape path for the balloon inflation media resulting in the balloon deflating in the vasculature. This is of special concern for neurovascular balloons, since such balloons are particularly small any minimal leakage can lead to balloon deflation which can negatively impact the intravascular procedure. Additionally, proper dispensation of inflation media is important to avoid overfilling or underfilling the balloon—this is especially critical with neurovascular balloons given the small size of the balloon.

The present invention addresses these and other issues by utilizing a purging system for a balloon catheter which does not lead to balloon deflation and utilizing metered dispensation for precise filling of the balloon with inflation media.

OBJECTS AND SUMMARY OF THE INVENTION

In one embodiment, the present invention includes a balloon catheter that is operable to use with large gauge guidewires, resists ovalizing and kinking of the inflation and guidewire lumen(s), and deploys with improved pushability and trackability.

The present invention according to another embodiment provides a balloon catheter that employs a reinforced, coaxial, duel lumen design. In certain embodiments, the lumens are formed of a multilayer, tubular element in which one of the layers functions, in part, to provide radial reinforcement to the tubular element.

In another embodiment of the present invention, the distal portion of an outer lumen is locked or fixed to a portion of an inner lumen. A proximal portion of a balloon is attached to a distal portion of the outer lumen and a distal portion of the balloon is attached to a distal portion of the inner lumen.

In another embodiment, a fluid flow passage is provided between the outer lumen and an interior volume of the balloon, and a passage exclusive to gas or air is formed from the interior volume of the balloon longitudinally through a distal portion of the balloon catheter.

In certain other embodiments, de-airing channels or features are employed between an exterior surface of the inner lumen and an interior surface of the balloon in order to facilitate purging of gas from the inflation passageway of the balloon catheter.

In other embodiments, leak-proofing systems can be included to mitigate or prevent the balloon from leaking and deflating during operation.

In another embodiment, a tapered inflation lumen is utilized. In another embodiment, a tapered guidewire lumen is utilized. In another embodiment, both the inflation lumen and guidewire lumen are tapered. The taper can be continuous throughout the lumen(s), or localized within a particular region of the lumen(s).

In another embodiment, a balloon catheter includes a membrane which selectively allows the passage of air but retains liquid. The use of this membrane can be beneficial for prepping a balloon catheter for use, where air is purged from the balloon before it is placed in the patient's vasculature.

In another embodiment, a syringe which allows metered dispensing of inflation media to a balloon in a balloon catheter is provided.

In another embodiment, a balloon catheter system includes a syringe which allows metered dispensing of inflation media and a membrane which selectively allows the passage of air but retains liquid, thereby allowing the user to purge air from the balloon but retain the inflation media within the balloon.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIG. 2 is a partial elevation view of a balloon catheter according to one embodiment of the present invention.

FIG. 3 is a cross-sectional view taken along line A-A of FIG. 1 of a balloon catheter according to one embodiment of the present invention.

FIG. 4A is a partial elevation view of an outer assembly of a balloon catheter according to one embodiment of the present invention.

FIG. 4B is a cross-sectional view taken along line C-C of FIG. 4A of an outer assembly of a balloon catheter according to one embodiment of the present invention.

FIG. 5A is a partial elevation view of an inner assembly of a balloon catheter according to one embodiment of the present invention.

FIG. 5B is a cross-sectional view taken along line D-D of FIG. 5A of an inner assembly of a balloon catheter according to one embodiment of the present invention.

FIG. 21b is a perspective view of the metered dispenser system of FIG. 21a.

FIG. 22b is a perspective view of the metered dispenser system of FIG. 22a.

DESCRIPTION OF EMBODIMENTS

Figure 1:
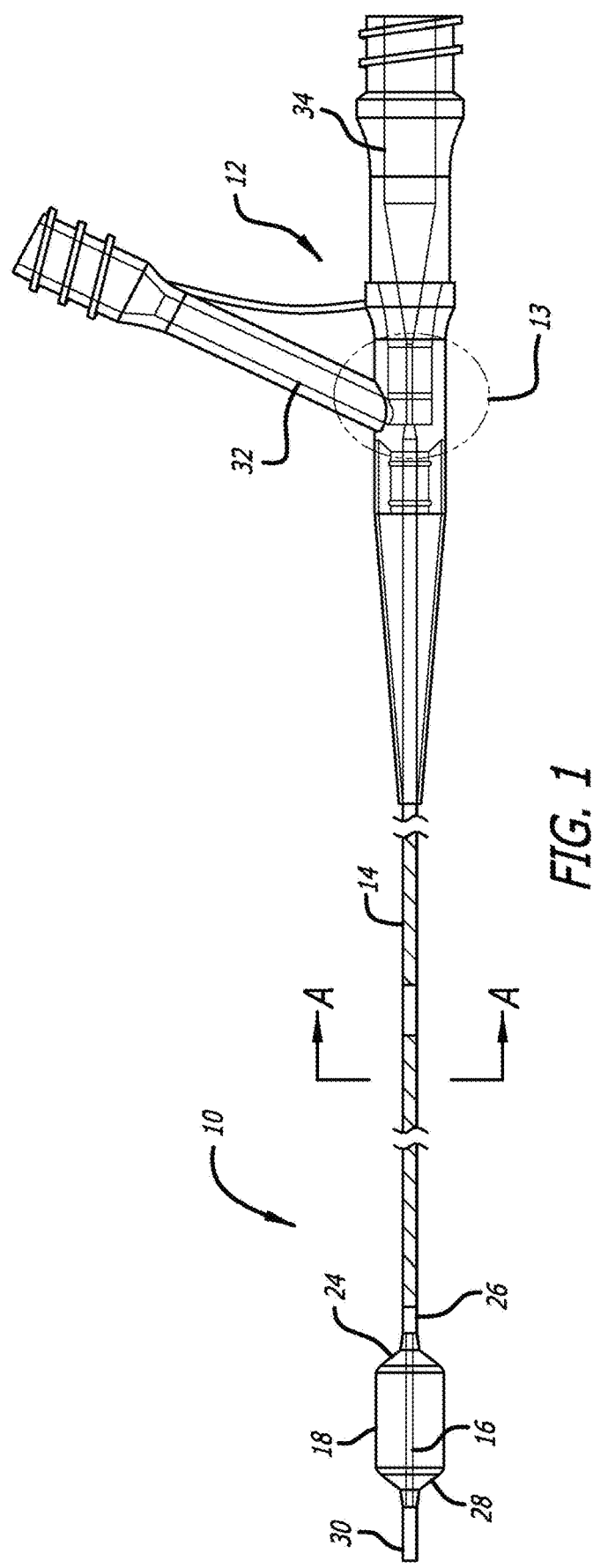
FIG. 1 is an elevation view of a balloon catheter according to one embodiment of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The balloon catheter of the present invention overcomes many of the shortcomings of the current balloon catheters intended for use in neurological procedures. Broadly speaking, the balloon catheter of the present invention employs a reinforced, co-axial, duel lumen design. The inner most lumen is operable to serve, among other functions, as a guidewire lumen for over-the-wire type procedures. The outer lumen is operable to serve as an inflation lumen for one or more balloons positioned along the length of the balloon catheter. Each lumen is formed by a multilayer, tubular element in which one of the layers, for example a middle layer in a three-layer embodiment, functions in part to provide radial reinforcement to the tubular element. Accordingly, the balloon catheter of the present invention is operable with larger gauge guidewires; resists ovalizing and kinking of the inflation and guidewire lumens; and deploys with improved pushability and trackability over current balloon catheters intended for use in neurological procedures.

Figure 6:
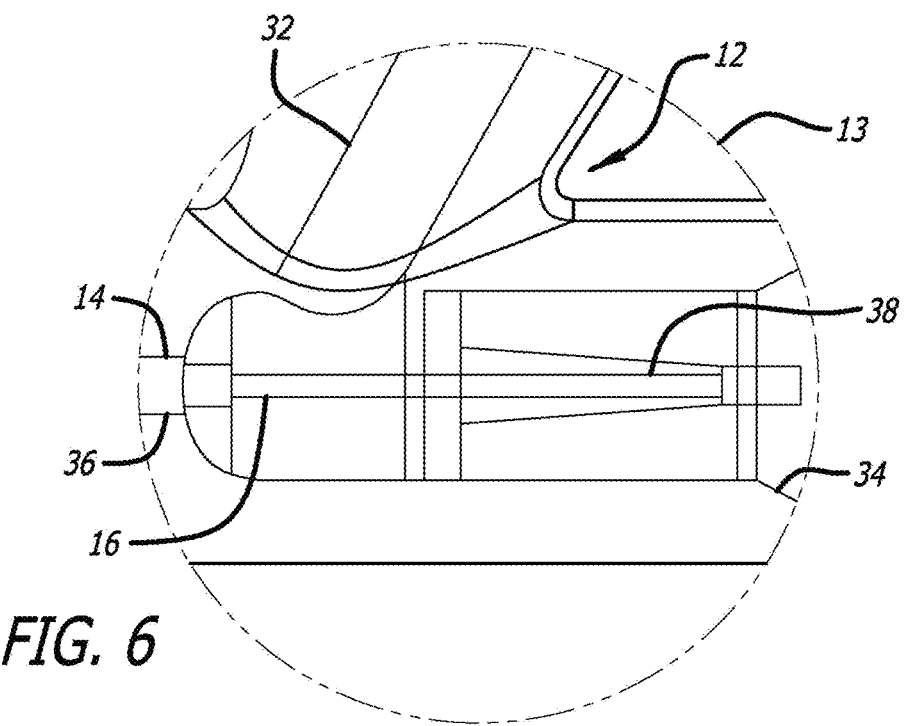
FIG. 6 is an expanded view of region 13 indicated in FIG. 1 of a balloon catheter according to one embodiment of the present invention.

With reference to FIGS. 1-3 and 6, a balloon catheter 10 according to one embodiment of the present invention comprises a hub 12, a balloon 18, and an outer assembly 14 having a lumen 20 through which an inner assembly 16 is co-axially positioned. As best shown in FIG. 6, an expanded view of region 13 indicated in FIG. 1, a proximal portion 36 of the outer assembly 14 is associated with an inflation lumen 32 of the hub 12. A proximal portion 38 of the inner assembly 16 extends proximally from the lumen 20 of the outer assembly 14 and is associated with a guidewire port 34 of the hub 12. At an opposite end of the catheter, a proximal portion 24 of the balloon 18 is associated with a distal portion 26 of the outer assembly 14, and a distal portion 28 of the balloon 18 is associated with a distal portion 30 of the inner assembly 16. Alternatively stated, the opposite ends of the balloon 18 span between the distal portion 26 of the outer assembly 14 and the distal portion 30 of the inner assembly 16.

As shown in FIGS. 4A and 4B, the outer assembly 14 is a tubular structure having a multilayer wall; an inner layer 40, a middle layer 42, and an outer layer 44. The inner layer 40 of the outer assembly 14 is formed of a longitudinally continuous or segmented tubular element. In embodiments in which the inner layer 40 of the outer assembly 14 is formed of longitudinally segmented tubular elements the individual segments may be fabricated from the same or different materials and may be attached to one another by welding, fusing, adhering, melting, or other polymerizing or non-polymerizing methods. The inner layer 40 of the outer assembly 14 is fabricated from one or more different polymeric materials, or, alternatively, the inner layer 40 of the outer assembly 14 is formed of a single etched polytetrafluoroethylene, PTFE, tube. While a variety of materials are contemplated for use in fabricating the inner layer 40 of the outer assembly 14, of particular importance is the feature that the material from which the inner layer 40 is formed has a higher melting temperature than the temperature employed to fuse or otherwise attach the outer layer 44 to the inner layer 40 and middle layer 42 of the outer assembly 14.

In one embodiment of the present invention, the middle layer 42 of the outer assembly 14 comprises a wire 46 wound in a coil-like form around the outer surface 48 of the inner layer 40 of the outer assembly 14. The wire 46 may be wound in a single layer from one end of the inner layer 40 to the other end to form a coil-like structure or, alternatively, may be wound repeatedly from one end of the inner layer 40 to the other end to form a multilayer coil-like form, as shown in FIG. 4A. In embodiments employing the middle layer 42 having a multilayered coil-like form, the different windings may be formed from a single or multiple independent wires 46. The wire 46 may have a circular, rectangular, triangular, or flattened ribbon-like cross-sectional shape, or combinations thereof. The wire 46 is fabricated from a variety of polymeric and/or metallic materials, for example stainless steel. The wire 72 has a diameter that is variable or consistent along the length of the wire 72. For example, the wire 72 may have a diameter of approximately 0.001 inches. It is also contemplated that the middle layer 42 be formed of a mesh, a braid, and/or an interweaving of one of more wires 46.

The pitch of the winding of the wire 46 may be either consistent or varied along the length of the inner layer 40. For example, a first proximal segment of the winding may have a pitch of approximately 0.003 inches, a second more distal segment may have a pitch of approximately 0.0035 inches, a third more distal segment may have a pitch of approximately 0.004 inches, a fourth more distal segment may have a pitch of approximately 0.0045 inches, a fifth more distal segment may have a pitch of approximately 0.005 inches, and a sixth more distal segment may have a pitch of approximately 0.001 inches. In embodiments employing the middle layer 42 having a multilayered coil-like form the outer most winding may, for example, have a pitch of approximately 0.100 inches.

In one embodiment of the present invention, the outer layer 44 of the outer assembly 14 comprises a longitudinally continuous or segmented tubular element. The outer layer 44 of the outer assembly 14 is formed of longitudinally segmented, non-heat shrinkable, tubular elements. The individual segments may be fabricated from the same or different materials and may be attached to one another by welding, fusing, adhering, melting, or other polymerizing or non-polymerizing methods, or combinations thereof.

In one embodiment, the outer layer 44 of the outer assembly 14 is fabricated from multiple different polymeric tubular segments. For example, a proximal segment 50 of the outer layer 44 of the outer assembly 14 may be formed of a tubular polyamide such as Grilamid L25. The proximal segment 50 has a length 51 of, for example, approximately 110 centimeters. A second more distal segment 52 may be formed of a tubular poly ether block amide such as Pebax 72D. The second more distal segment 52 has a length 53 of, for example, approximately 10 centimeters. A third more distal segment 54 may be formed of a tubular poly ether block amide such as Pebax 63D. The third more distal segment 54 has a length 55 of, for example, approximately 5 centimeters. A forth more distal segment 56 may be formed of a tubular poly ether block amide such as Pebax 55D. The forth more distal segment 56 has a length 57 of, for example, approximately 20 centimeters. A fifth more distal segment 58 may be formed of a tubular poly ether block amide such as Pebax 45D. The fifth more distal segment 58 has a length 59 of, for example, approximately 10 millimeters. A sixth more distal segment 60 may be formed of a polyolefin such a Plexar. The sixth more distal segment 60 has a length 61 of, for example, approximately 2 millimeters. A distal most segment 62 may be formed of a polyolefin such an Engage 8003. The distal most segment 62 has a length 63 of, for example, approximately 13 centimeters.

The outer assembly 14 may be fabricated by first wrapping the wire 46 around the inner layer 40 thereby forming the middle layer 44. The tubular segment or segments of the outer layer 44 are then slid over the middle layer 42. A heat shrinkable tube of, for example, fluorinated ethylene propylene, FEP, is then slid over the outer layer 44. The FEP is heated so as to deliver heat to the outer layer 44, and the outer layer 44 then softens to encapsulate the wire 46. The FEP tube is then removed from the outer layer 44.

In one embodiment of the present invention, the outer diameter of the outer layer 44 of the outer assembly 14 is in the range of 0.03 to 0.040 inches. The lumen 20 of the outer assembly 14 may have a diameter between 0.020 to 0.029 inches. In one embodiment, the lumen 20 of the outer assembly 14 may have a diameter of approximately 0.0285 inches.

As shown in FIGS. 5A and 5B, the inner assembly 16 is a tubular structure having a multilayer wall formed of an inner layer 64, middle layer 66, and outer layer 68. The inner layer 64 of the inner assembly 16 is formed of a longitudinally continuous or segmented tubular elements. In embodiments in which the inner layer 64 of the inner assembly 16 is formed of longitudinally segmented tubular elements, the individual segments may be fabricated from the same or different materials and may be attached to one another by welding, fusing, adhering, melting, or other polymerizing or non-polymerizing methods, or combinations thereof. The inner layer 64 of the inner assembly 16 is fabricated from one or more different polymeric materials, or, alternatively, the inner layer 64 of the outer assembly 14 is formed of a single, non-segmented, etched polytetrafluoroethylene, PTFE, tube. While a variety of materials are contemplated for use in fabricating the inner layer 64 of the inner assembly 16, it is important to employ a material that has a higher melting temperature than the temperature employed to fuse or otherwise attach the outer layer 68 to the inner layer 64 and middle layer 66 of the inner assembly 16. It is also desirable to employ a material that has a relatively low co-efficient of friction.

In one embodiment of the present invention, the middle layer 66 of the inner assembly 16 comprises a wire 70 wound in a coil-like form around the outer surface 72 of the inner layer 64 of the inner assembly 16. The wire 72 may be wound in a single layer from one end of the inner layer 64 to the other or, alternatively, may be wound repeatedly from one end of the inner layer 64 to the other to form a multilayer coil-like form, as shown in FIG. 4A regarding wire 46 of the outer assembly 14. In embodiments employing the middle layer 66 having a multilayered coil-like form, the different coils may be formed from a single or multiple independent wires 72. The wire 72 may have a circular, rectangular, triangular, flattened, ribbon-like cross-sectional shape, or a combination thereof. The wire 72 may be fabricated from a variety of metallic and/or polymeric materials, for example stainless steel. The wire 72 may have a diameter that is variable or consistent along the length of the wire 72. For example, the wire 72 may have a diameter of approximately 0.001 inches. It is also contemplated that the middle layer 42 may be formed of a mesh or interweaving of one of more wires 46.

The pitch of the winding of the wire 72 may be either consistent or varied along the length of the inner layer 64 of the inner assembly 16. For example, a first proximal segment of the wire 72 winding may have a pitch of approximately 0.003 inches, a second more distal segment may have a pitch of approximately 0.003 inches, and a third most distal segment may have a pitch of approximately 0.001 inches.

As shown in FIGS. 2 and 5A, in one embodiment of the present invention, one or more marker bands 82A, 82B, and 82C are placed, for example, over the wire 70 forming the middle layer 66 of the inner assembly 16. The marker bands 82A, 82B, and 82C comprise a radiopaque material such as gold, platinum, or silver, and are used for determining the location of the balloon catheter 10 within a patient. In certain embodiments of the present invention the maker band 82A may be placed a distance L3 proximate to a distal end 86 of the inner assembly 16. For example, the distance L3 may be 5 millimeters. In one embodiment, instead of marker bands, marker coils may be used. In one embodiment, two sets of marker coils are used where one coil overlaps another to augment the radiopacity of the marker elements.

The marker bands 82B and 82C may be positioned further proximal of the marker band 82A so as to indicate or mark the proximal portion 24 and the distal portion 28 of the balloon 18. It will be understood that the exact placement of the marker bands 82B and 82C relative to the distal end 86 of the inner assembly 16 will depend on the dimensions of the balloon 18 employed in the balloon catheter 10.

For example, in an embodiment employing a balloon 18 of 10 millimeters in length, a proximal end 84 of the marker band 82C is a distance L1 from the distal end 86 of the inner assembly 16. For example, the distance L1 may be approximately 19.5 millimeters. Opposite ends of the marker bands 82B and 82C are a distance L2 from one another. For example, the distance L2 may be 10 millimeters. In an embodiment employing a balloon 18 of 20 millimeters in length, the distance L1 is, for example, approximately 29.5 millimeters, and the distance L2 is, for example, 20 millimeters. In another embodiment, the marker band 82C may be placed directly underneath the inflation plug 88.

In one embodiment of the present invention, the outer layer 68 of the inner assembly 16 comprises a longitudinally continuous or segmented tubular element. Preferably the outer layer 68 of the inner assembly 16 is formed of series of longitudinally segmented, non-heat shrinkable, tubular elements. The individual segments are fabricated from the same or different materials and may be attached to one another by welding, fusing, adhering, melting, or other polymerizing or non-polymerizing methods. Preferably, the outer layer 68 of the inner assembly 16 is fabricated from multiple different polymeric tubular segments. For example, a proximal segment 74 of the outer layer 68 of the inner assembly 16 may be formed of a tubular poly ether block amide such as Pebax 63D. The proximal segment 74 has a length 75 of, for example, approximately 150 centimeters. A second more distal segment 76 may be formed of a tubular polyether block amide such as Pebax 45D. The second more distal segment 76 has a length 77 of, for example, approximately 10 centimeters. A third more distal segment 78 may be formed of a polyolefin such as Plexar 3080. The third more distal segment 78 has a length 79 of, for example, approximately 2 millimeters. A distal most segment 80 may be formed of a polyolefin such as Engage 8003, and have a length 81 of, for example, approximately 5 centimeters.

The inner assembly 16 may be fabricated by first wrapping the wire 70 around the inner layer 64 thereby forming the middle layer 66. Next, the marker bands 82A, 82B, and 82C are placed over or within the middle layer 66, and the tubular segment or segments of the outer layer 68 are then slid over the marker bands 82A, 82B, and 82C and the middle layer 66. A heat shrinkable tube of, for example, fluorinated ethylene propylene, FEP, is then slid over the outer layer 68. The FEP is heated so as to deliver heat to the outer layer 68, thereby softening the outer layer 68 so as to encapsulate the wire 70 forming the middle layer 66. The FEP tube is then removed from the outer layer 68.

In one embodiment of the present invention, the wire 70 forming the middle layer 66 of the inner assembly 16 may terminate proximal of the distal end 86 of the outer assembly 16. A tubular element 100 may be employed in all or a portion of the length between the distal end 86 and the point at which the wire 70 terminates. The tubular element 100 may, for example, be formed of a crosslinked polyolefin tube having a length of approximately 5 millimeters.

In one embodiment of the present invention, the outer diameter of the outer layer 68 of the inner assembly 16 is in the range of 0.015 to 0.025 inches, and more preferably in the range of 0.020 to 0.0225 inches.

Figure 5C:
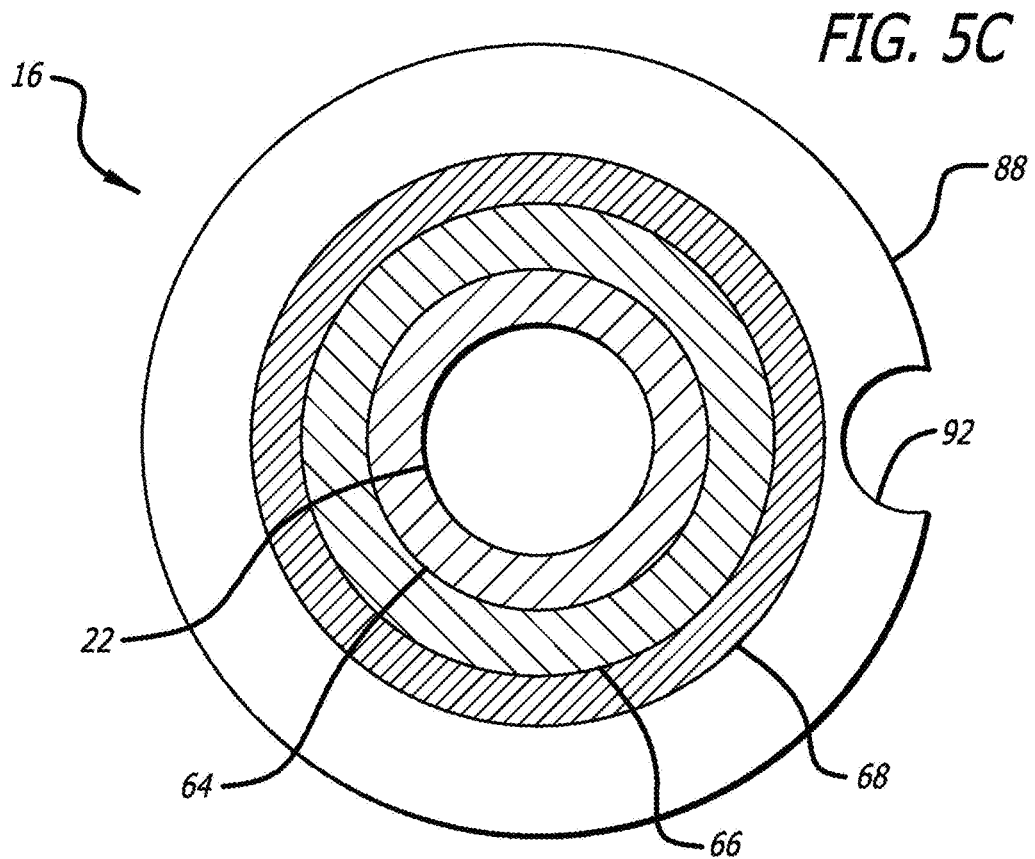
FIG. 5C is a cross-sectional view taken along line E-E of FIG. 5A of an inner assembly of a balloon catheter according to one embodiment of the present invention.

As shown in FIGS. 2, 5A, and 5C, in one embodiment of the present invention, the inner assembly 16 may further comprise an inflation plug 88. The inflation plug 88 is formed of a tubular segment of material having a wall of either uniform or asymmetric thickness. In some embodiments, the inflation plug may have a durometer ranging between 18A to 55D. The inflation plug 88 may, for example be formed of a poly ether block amide such as Pebax 55D. The inflation plug may, for example, be approximately 5 millimeters in length and a distal end 90 of the inflation plug 88 may, for example, be positioned approximately 4 millimeters from the proximal end 84 of the marker band 82C. An outer dimension or diameter of the inflation plug 88 is large enough so that the inflation plug 88 may not completely pass into the lumen 20 of the outer assembly without significant force. The inflation plug 88 may be formed on the inner assembly 16 as described above regarding the formation of the outer layer 68 of the inner assembly 16.

As shown in FIG. 5C, the inflation plug 88 may comprise one or more passages or channels 92 formed longitudinally along the length of the inflation plug. The channel 92 may be formed by placing a mandrel longitudinally along the outside surface of the inflation plug 88 prior to sliding the heat shrinkable tube of, for example, FEP over the inflation plug 88. When the FEP is heated so as to deliver heat to the inflation plug 88, the mandrel melts into the inflation tube thereby the channel 92 within the inflation plug 88. The FEP tube is then removed from the inflation plug 88.

The inflation plug 88 functions, in part, to longitudinally lock the inner assembly 16 to the outer assembly 14 so as to prevent changes in the length of the distal extension of the distal portion 30 of the inner assembly 16 relative to a distal end 98 of the outer assembly 14 due to the inflation and orientation of the balloon 18 during a procedure. The passage or channel 92 formed in the plug 88 allows for fluid communication between the lumen 20 of the outer assembly and an interior volume of the balloon 18.

As shown in FIGS. 3, 5B, 5C, and 7, the inner assembly 16 comprises an inner lumen 22. The lumen functions as a guidewire lumen for over-the-wire procedures. The lumen 22 of the inner assembly 16 may have a diameter of at least approximately 0.0165 inches. Accordingly, the balloon catheter 10 of the present invention may be used with guidewires having a larger diameter than the guidewires supplied with current balloon catheters intended for use in neurological procedures. For example, the present balloon catheter 10 may be used with a guidewire having a diameter of 0.014 inches. This feature allows a physician to more easily access a neuroanatomical target, such as an aneurysm, since the relatively larger guidewire provides more support for the balloon catheter 10 over which to track.

Additionally, the guidewire may be removed from the lumen 22 after placement of the balloon catheter within a patient and the lumen 22 may serve as a functional lumen for passage of additional medical devices or substances to the target location within the patient.

It will be understood that it is generally beneficial for the outer assembly 14 and the inner assembly 16 to be more flexible at their distal portions than their proximal portions. Furthermore, it is contemplated that the distal portions of the outer assembly 14 and/or the inner assembly 16 may be pre-shaped or operable to be shaped by a physician prior to initiating a procedure using, for example, steam shaping techniques.

As shown in FIGS. 1 and 6, the proximal portion 36 of the outer assembly 14 terminates distally of the proximal portion 38 of the inner assembly 16. Accordingly, the lumen 20 of the outer assembly is in communication with the inflation port 32. FIGS. 1 and 6 also show that the proximal portion 38 of the inner assembly 16 extends proximally beyond the proximal portion 36 of the outer assembly 14 and is associated with the guidewire port 34 of the hub 12. Accordingly, the lumen 22 of the inner assembly and the guidewire port 34 of the hub 12 together form a substantially continuous lumen through which a guidewire or other medical device may pass. The outer assembly 14 and the inner assembly 16 may be attached to the hub 12 by various methods, including welding, fusing, adhering, melting, or other polymerizing or non-polymerizing method, or combinations thereof. It is noted that this configuration of the hub 12 and association of the hub 12 with the outer assembly 14 and the inner assembly 16 advantageously provides for the isolation of the lumen 22 of the inner assembly 16 from the lumen 20 of the outer assembly 14. The isolation of these lumens and their functionality serves, in part, to address many of the shortcomings described above regarding the current single lumen balloon catheters intended for neurological procedures.

As shown in FIGS. 1 and 2, the proximal portion 24 of the balloon 18 is associated with the distal portion 26 of the outer assembly 14, and the distal portion 28 of the balloon 18 is associated with the distal portion 30 of the inner assembly 16. The balloon 18 may be attached to the distal portion 26 of the outer assembly 14 and the distal portion 30 of the inner assembly 16 by various methods including welding, fusing, adhering, melting, or other polymerizing or non-polymerizing methods and combinations thereof. In certain embodiments, the distal portion of the balloon 18 covers and extends to the distal end 86 of the inner assembly 16. The balloon 18 may, for example, be formed of Polyblend 45A or other polymeric elastomeric material. The balloon 18 may have an outer diameter of up to approximately 15 millimeters and a length in the range of 5 to 50 millimeters and, preferably a length in the range of 10 to 20 millimeters.

Figure 7:
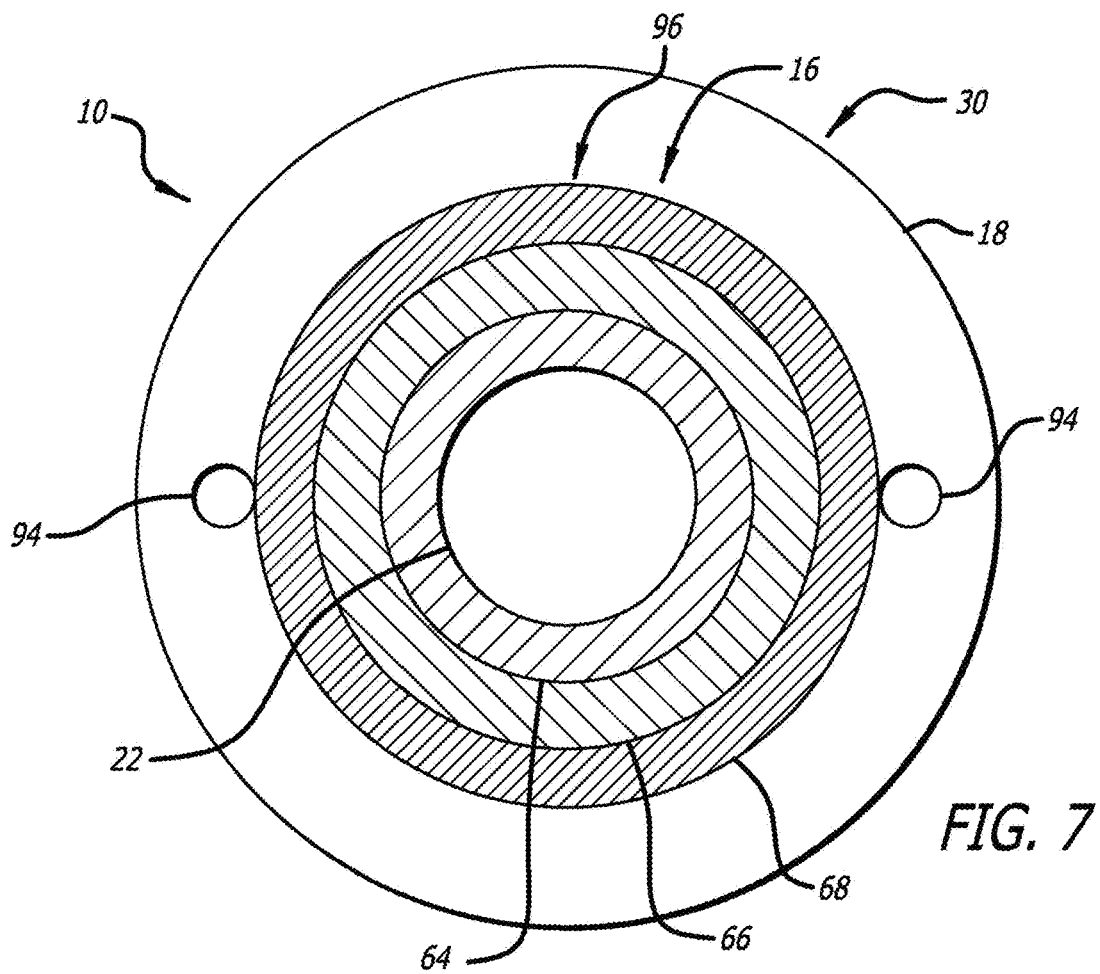
FIG. 7 is a cross-sectional view taken along line B-B of FIG. 2 of an inner assembly of a balloon catheter according to one embodiment of the present invention.

As shown in FIG. 7, in one embodiment of the present invention, one or more air purge ports 94 are employed at the interface of the distal portion 30 of the inner assembly 16 and the distal portion 28 of the balloon 18. The air purge ports 94 are formed by placing one of more mandrels having diameters in the range of 0.0005 to 0.030 inches on the outer surface of the outer layer 68 of the inner assembly 16. An interior surface 96 of the balloon 18 is then attached over the mandrels to the outer layer 68 of the inner assembly 16. After the balloon 18 is attached to the distal portion 30 of the inner assembly 16 the mandrels are removed. Accordingly, flow paths large enough for the passage of gas and small enough to seal against the passage of liquids are formed.

The air purge ports 94 function to facilitate removal of air from the lumen 20 and balloon 18 prior to initiating a medical procedure. With current co-axial balloon catheters, it is very difficult to remove all of the air from the inflation/deflation lumen prior to initiating a medical procedure. Physicians typically must remove the air from a balloon catheter through several minutes of aspiration or suction through the inflation/deflation lumen. Air that is not removed will show in images taken during the procedure and may obscure details that the physician may otherwise need to observe in order to perform the procedure.

In contrast, the air purge ports 94 of the present invention allow a user to more effectively and more efficiently remove air from the lumen 20, the inflation/deflation lumen. In practice, prior to initiating the procedure, a physician positions the distal end of the balloon catheter 10 higher than the proximal end and then injects a balloon inflation medium, such as contrast medium or saline, through the inflation port 32 and associated lumen 20. As the inflation medium fills the lumen 20, air is forced out the air purge ports 94 until no air remains within the lumen 20 or balloon 18. The physician may repeat the process as needed to ensure that all air is removed from the lumen 20 of the outer assembly 14 and balloon 18.

Figure 8:
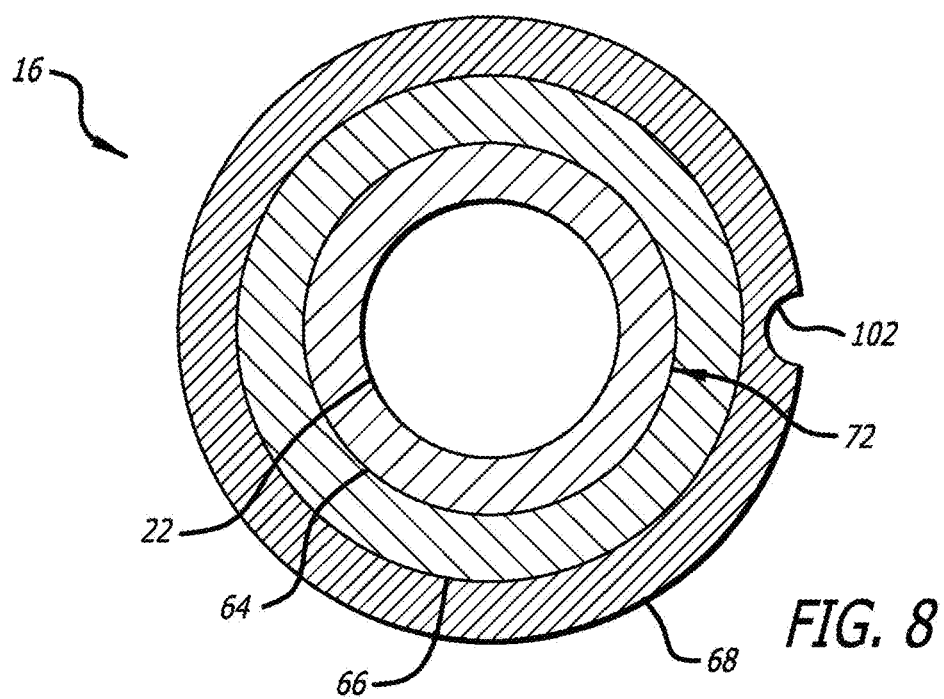
FIG. 8 is a cross-sectional view taken along line D-D of FIG. 5A of an inner assembly of a balloon catheter according to one embodiment of the present invention.
Figure 9:
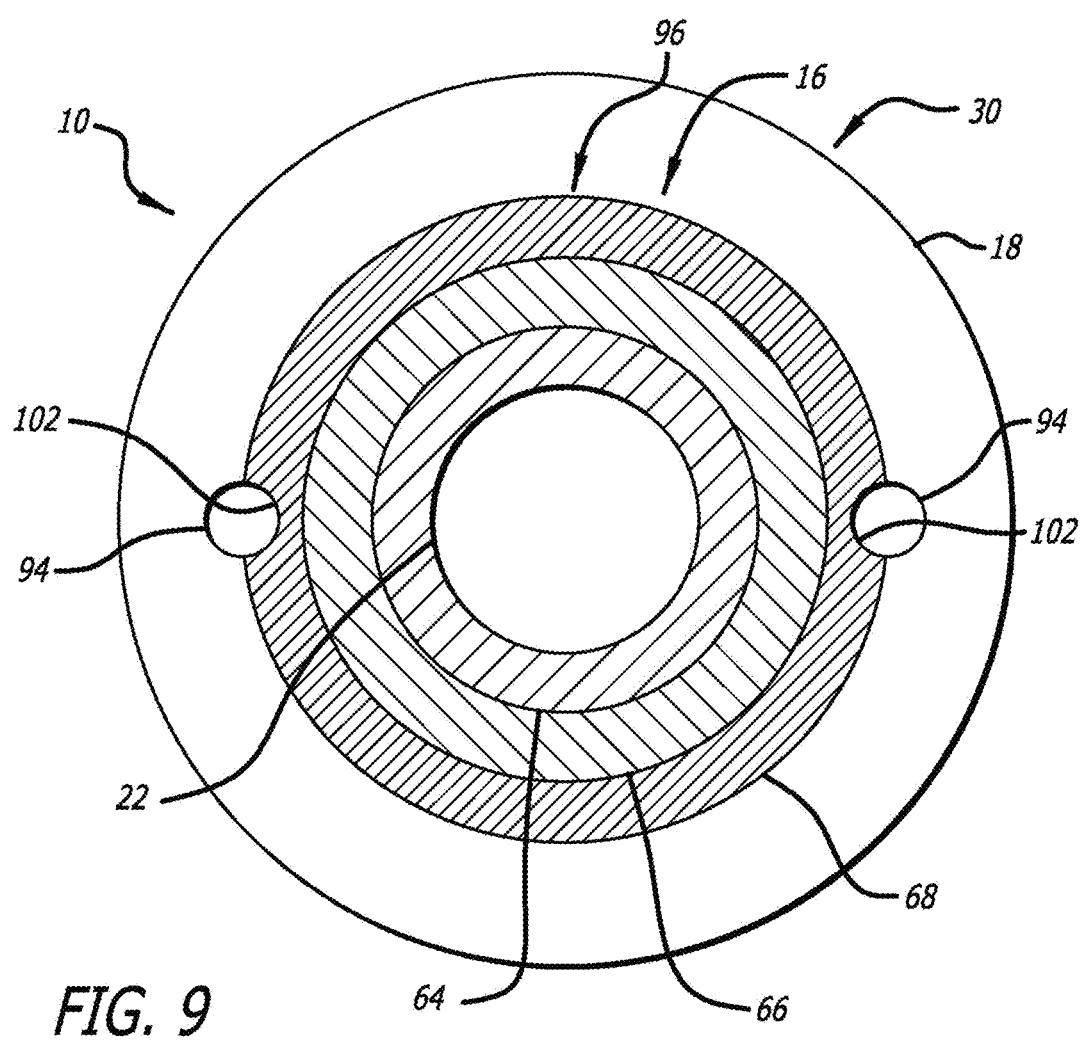
FIG. 9 is a cross-sectional view taken along line B-B of FIG. 2 of an inner assembly of a balloon catheter according to one embodiment of the present invention.

In another embodiment of the present invention, as shown in FIGS. 8 and 9, the above described functionality of the inflation ports 32 is enhanced by employing one or more de-airing channels 102. The de-airing channel 102 is formed in the outer layer 68 of the inner assembly 16. At a minimum, the de-airing channel 102 initiates longitudinally approximate the distal end 90 of the inflation plug 88 and continues uninterruptedly to approximately a proximate end of the air purge port 94. The length of the de-airing channel 102 may extend to or overlap with the distal end 90 of the inflation plug 88 and/or the proximate end of the air purge port 94. The de-airing channel 102 may be either radially aligned or radially off set with the channel 92 of the inflation plug 88 and/or the air purge port 94 relative to an axis through the lumen 22 of the inner assembly 16.

The de-airing channel 102 is formed by placing one of more mandrels having diameters in the range of 0.001 to 0.030 inches between the outer layer 68 of the inner assembly 16 and the heat shrinkable tube and then heating the heat shrinkable tube as described above. In certain embodiments, the de-airing channel 102 is radially aligned with the air purge port 94 and/or with the channel 92 formed in the inflation plug 88. For example, FIG. 9 shows an embodiment in which the de-airing channel 102 is radially aligned with the air purge port 94. The de-airing channel 102 and the air purge port 94 each form a portion of a unified channel. In embodiments in which the de-airing channel 102 is radially aligned with the air purge port 94 and/or with the channel 92 formed in the inflation plug 88, the de-airing channel 102 may extend longitudinally the length of the air purge port 94 and/or may extend longitudinally into or proximately beyond the channel 92 formed in the inflation plug 88.

The de-airing channel 102 helps ensure that a fluid and air flow path is maintained unobstructed between the exterior surface of the inner assembly 16 and the interior surface 96 of the balloon 18. Because the balloon 18 may be closely form fitted over the inner assembly 16 when the balloon is not inflated, absent a de-airing channel 102, it may not always be possible to purge air from lumen 20 of the outer assembly 14 without inflating the balloon 18. Hence, the de-airing channel 102 provides a recess or unobstructed channel on the exterior surface of the inner assembly 16 that allows the passage of air and fluid between the deflated balloon and the exterior surface of the inner assembly 16. Hence, air may be purged from the balloon catheter 10 without inflating of the balloon 18.

It is also contemplated that the de-airing channel 102 may take the form of one or more spiral channels or grooves, spiral ridges, and/or longitudinal ridges on the exterior surface of the inner assembly 16. The de-airing channel 102 may also take the form of one or more small tubular elements bonded to the exterior surface of the inner assembly 16.

In the following embodiments shown in FIGS. 10-18, the purge port 94 is located at a distal interior portion of an inflatable portion of the balloon 18 and is intended to represent an opening or an area of an opening and the de-airing channel 102 links the distal purge port 94 to an exterior of the distal end of the balloon catheter. Accordingly, air is conveyed distally from purge port 94 through de-airing channel 102 and out of the distal end of the balloon catheter. The purge port 94 is therefore the proximal entry point for air, where the air is then conveyed distally through de-airing channel 102. All the purging of air from the interior of the balloon is performed at the distal portion of the balloon catheter. The inflation lumen remains located proximal to the balloon 18; therefore, the balloon 18 is inflated from the proximal end while all the purging is performed at the distal section of the balloon 18. As described in the following embodiments, de-airing channel 102 is initially open to purge air from the balloon 18 during a first, preparation stage; de-airing channel 102 is later sealed in a second, operational state to prevent the balloon from leaking when the balloon is used in an inflated state during an interventional procedure. In these embodiments purge port 94 represents a proximal opening, located within the balloon, into de-airing channel 102. An opposite, distal end of the de-airing channel 102 is located at the distal end of the balloon catheter.

One embodiment of the present invention includes a swellable material along with the previously described purge port and the de-airing channel arrangement. The swellable material swells in response to exposure to certain materials, such as liquids, and thereby closes the de-airing channel to block passage of liquids. It may be desirable to selectively allow the de-airing channel to initially be open to purge air, but to then close upon exposure to liquid (such as saline or contrast agent) to prevent liquid escaping from the balloon in order to keep the balloon inflated over time. In one example, the user flushes the system with contrast agent to expel air and prepare the balloon for use. Contrast agent is also used to inflate the balloon during use. Once the air is purged out of de-airing channel, the de-airing channel closes upon exposure to contrast agent to prevent contrast agent from later escaping once additional contrast agent is later introduced to inflate the balloon (e.g. once the balloon is later inflated in the body during the interventional procedure).

The swellable material can be used either on or over a portion of de-airing channel or can be placed adjacent to de-airing channel, for example near purge port 94. A hydrophilic material will swell upon exposure to liquid (e.g. saline or contrast agent) and closes the de-airing channel once the section of the de-airing channel containing the hydrophilic swellable material is exposed to liquid. The de-airing channel, therefore, stays open as air is expelled through the port; however, once de-airing channel contacts the liquid (e.g., in a situation where the air is almost completely flushed from the balloon/balloon catheter and now liquid is being expelled), de-airing channel will swell causing the internal passage to contract, blocking the liquid from being expelled. Various hydrophilic materials such as rubber or hydrogel can be used as the swellable material.

Figure 10:
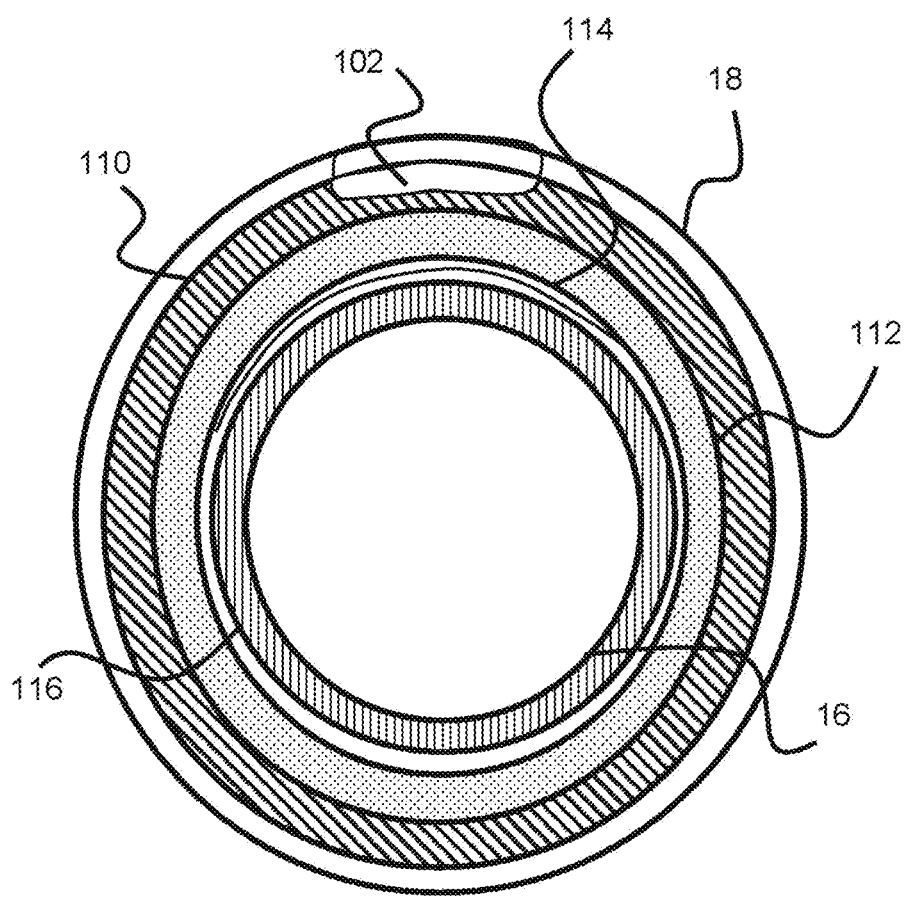
FIG. 10 is a cross-sectional view of a balloon catheter with a collapsible purge port according to one embodiment of the present invention.

The swellable material may be located adjacent de-airing channel or may physically comprise a particular section (e.g., the distal section) of de-airing channel. FIG. 10 shows such a system, utilizing a swellable material adjacent the de-airing channel 102. Specifically, FIG. 10 illustrates a cross sectional view of an embodiment of the present balloon catheter near the distal end of the balloon 18, where the de-airing channel 102 spans a distal, non-inflatable portion of the balloon 18. A swellable layer 110 is located under the de-airing channel 102, in addition to the optional additional liner layers 112, 114, 116, which can be located between the guidewire lumen 16 and the swellable layer 110. Alternatively, the swellable material can be used with any of the prior purge/de-airing system embodiments.

Alternative configurations may position the swellable material on a distal section of de-airing channel, thereby allowing the de-airing channel to contract upon exposure to liquid instead of having an adjacent surface compressing the de-airing channel. Alternatively, the swellable material can be utilized over the entire length of de-airing channel. Alternatively, the swellable material may be placed at the proximal end of de-airing channel or even at the purge port.

In another embodiment, the de-airing channel is collapsible. De-airing channel has a first, open configuration but collapses to adopt a second, closed configuration in response to a stimulus such as aspiration or a vacuum. The user prepares the balloon by introducing an agent (e.g., saline or contrast agent) to clear the air from the balloon. Next, the user introduces a vacuum or aspiration source which causes the de-airing channel to collapse and thereby shut. Later in the procedure, when the balloon is positioned in the body, the de-airing channel will remain sealed and the inflation media (e.g. contrast agent) will not escape, preventing the balloon from deflating over time.

A soft, tacky, and collapsible material can be used to create the de-airing channel 102 to enable the channel to easily collapse. An elliptical cross sectional shape may be desirable for such a system so that the minor axis of the ellipse requires only minor movement to collapse completely, although a more rounded shape may also be used where the de-airing channel walls are composed of a relatively weak polymer material that allows easy collapse. Additional cross sectional shapes, such as a "D" or a "C" shape, are also possible. In these example shapes, the flat side of the "D" shape or the open portion of the "C" shape can be oriented such that they are either facing a direction toward the guidewire lumen 16 or facing away from the guidewire lumen 16 (e.g., facing "downward" or "upward" in the example cross section of FIG. 10).

Figure 11:
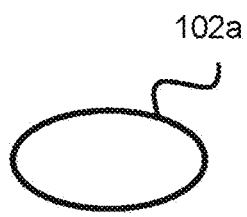
FIG. 11 is a cross-sectional view of a collapsible purge port in an open configuration according to one embodiment of the present invention.
Figure 12:
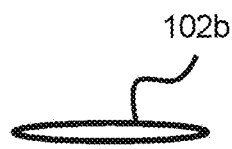
FIG. 12 is a cross-sectional view of a collapsible purge port in a closed configuration according to one embodiment of the present invention.

In one example, the entire length of de-airing channel is collapsible. In another example, only a section of de-airing channel is collapsible. In another example, only the purge port (which links to the de-airing channel) is collapsible. This collapsible section may be accomplished by a variety of methods, such as creating a weakened wall region in a section of the channel, thus allowing that section to easily constrict. FIGS. 11 and 12 show a cross-section of a collapsible de-airing channel in which the channel has a first open configuration 102*a* when the channel is open to purge the system, and the channel subsequently adopts a second closed configuration 102*b* once vacuum or aspiration is used to close all of the channel or a weakened section of the channel.

In another embodiment, the de-airing channel includes a restricting member positioned at or past the proximal end of the de-airing channel to block fluid flow at the proximal part of the de-airing channel once the balloon has been collapsed over the de-airing channel, thereby preventing over-aspiration. This restricting member may be a wall region having an increased thickness and located at the proximal end of the de-airing channel to block the channel lumen. This restricting member can also be described as a bump or protruding region which blocks access to the purge port and the de-airing channel. In operation, the user aspirates to deflate the balloon, however over-aspiration (the condition where suction or aspiration continues after the balloon is fully deflated) is undesirable since blood could be introduced into the balloon catheter. The bump seals de-airing channel preventing over-aspiration.

Figure 13:
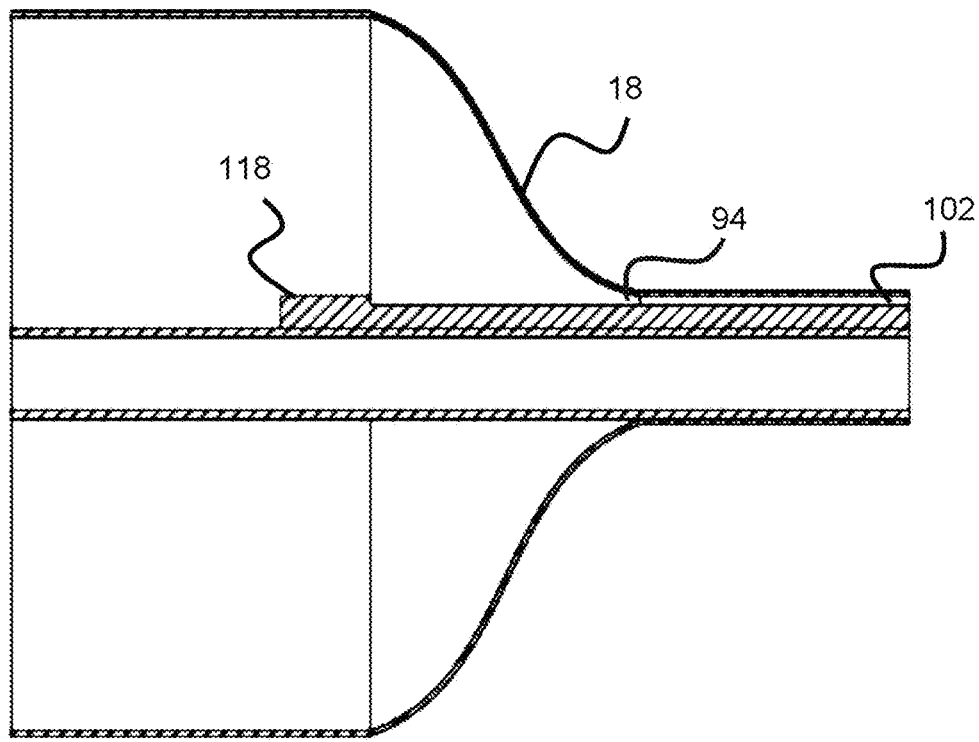
FIG. 13 is a cross-sectional view of a balloon catheter utilizing a bump to prevent access to a purge port according to one embodiment of the present invention, where the balloon is inflated.
Figure 14:
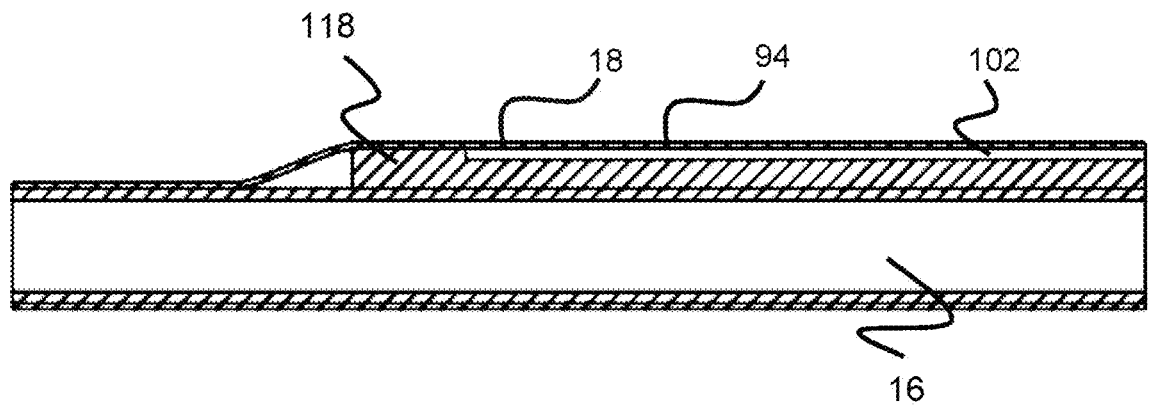
FIG. 14 is a cross-sectional view of a balloon catheter utilizing a bump to prevent access to a purge port according to one embodiment of the present invention, where the balloon is deflated.

This configuration is shown in FIGS. 13 and 14, where the right side represents the distal end of the balloon and the de-airing channel 102 spans from a distal, interior, inflatable section of the balloon 18 to the distal tip or end of the balloon catheter. In FIG. 13, the balloon is inflated and a bump 118 does not impede fluid flow since the balloon 18 is inflated and there is space for the fluid to pass. In FIG. 14 the balloon 18 is deflated, such as after the user has aspirated the balloon 18 to deflate it. In the deflated state, the bump 118 blocks the fluid flow path to the purge port 94 and the de-airing channel 102, so once the balloon 18 is completely deflated, further aspiration or suction is not possible.

Figure 15:
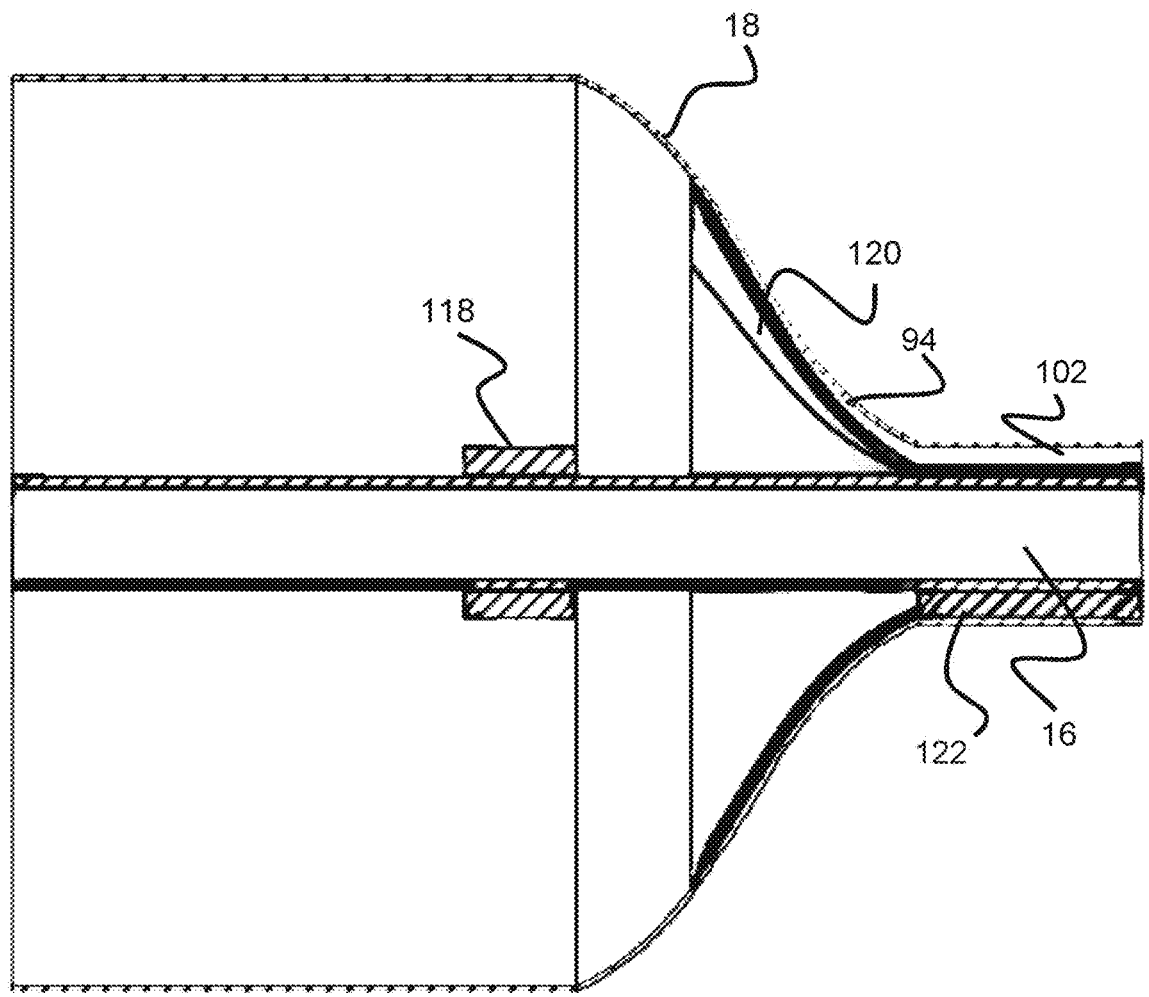
FIG. 15 is a cross-sectional view of a balloon catheter with a closable purge port and a bump according to one embodiment of the present invention, where a balloon is inflated.
Figure 16:
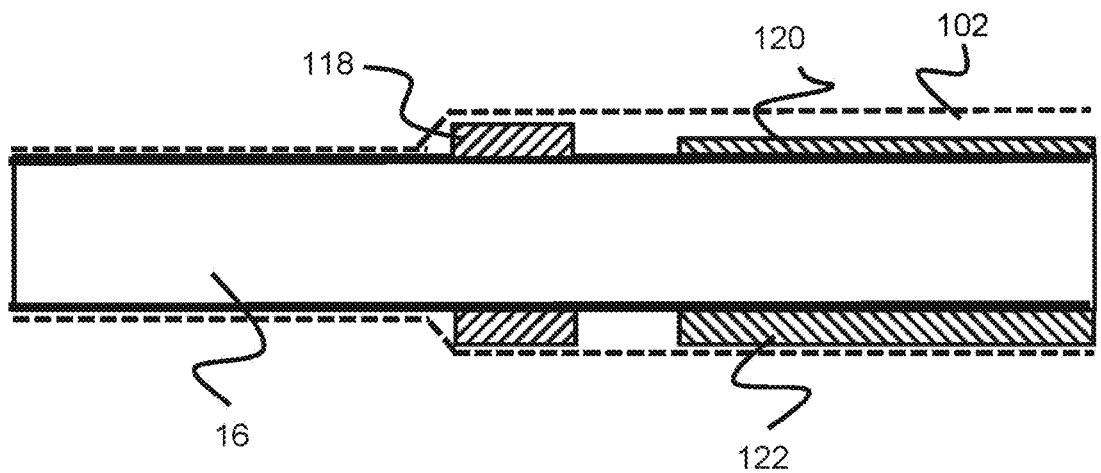
FIG. 16 is a cross-sectional view of a balloon catheter with a closable purge port and a bump according to one embodiment of the present invention, where a balloon is deflated.

In another embodiment shown in FIGS. 15 and 16, the de-airing channel 102 seals itself when the balloon 18 is fully inflated, to prevent any leakage from the balloon 18. In this embodiment, the distal section of the de-airing channel 102 is integral with the distal portion of the balloon wall. In other words, the wall of the balloon 18 contains a lumen which defines the de-airing channel, where the proximal lumen opening into de-airing channel 102 can be considered the purge port 94. This may be made in a number of ways, for example, the de-airing channel 102 may be first constructed utilizing a mandrel and then the balloon can be built over the de-airing channel 102 passage so that the de-airing channel 102 is incorporated into the distal section of the balloon 18; meaning the distal portion of the balloon 18 will include the de-airing channel 102 incorporated into the wall of balloon 18.

Alternately, the balloon can be built and then a mandrel can be placed within the balloon to form a lumen, where said lumen would define the de-airing channel. The wall of the balloon will stretch and will thin as the balloon inflates. This stretching and thinning action will compress a portion of the de-airing channel, which is incorporated into the balloon wall, causing the de-airing channel to close. Thus, when the balloon is fully inflated, the de-airing channel will close preventing any leakage. In an alternative configuration, a reinforcing band attached to the balloon may also be utilized to create a choke point on the distal section of the balloon. As the balloon expands, the band applies force on the section of the de-airing channel directly under the band since the distal de-airing channel is integrated into the balloon wall, which creates a choking point and closes a section of the de-airing channel.

Similar to the compressible de-airing channel embodiment above which utilizes an elliptical, or C-shaped, or D-shaped cross sectional de-airing channel shape to aid the self-closing of the de-airing channel, this embodiment may also utilize these channel shapes to further enable easier closing of the channel. The bump feature of FIGS. 13 and 14 may also be used to create a system that would prevent balloon leakage when the balloon is inflated as well as prevent over-aspiration once the balloon is deflated. This is presented in FIGS. 15 and 16, where de-airing channel 102 is integral with the balloon 18 wall. In one example, the balloon 18 utilizes liners 120, 122 which connect to part of the de-airing channel 102. As the balloon 18 expands, the liners compress against de-airing channel 102 causing the channel to close—as shown in FIG. 15, where the proximal section of the de-airing channel 102 tapers down to the point it is completely shut. When the balloon 18 is deflated as shown in FIG. 16, the de-airing channel 102 opens and the bump 118 prevents over-aspiration.

Figure 17:
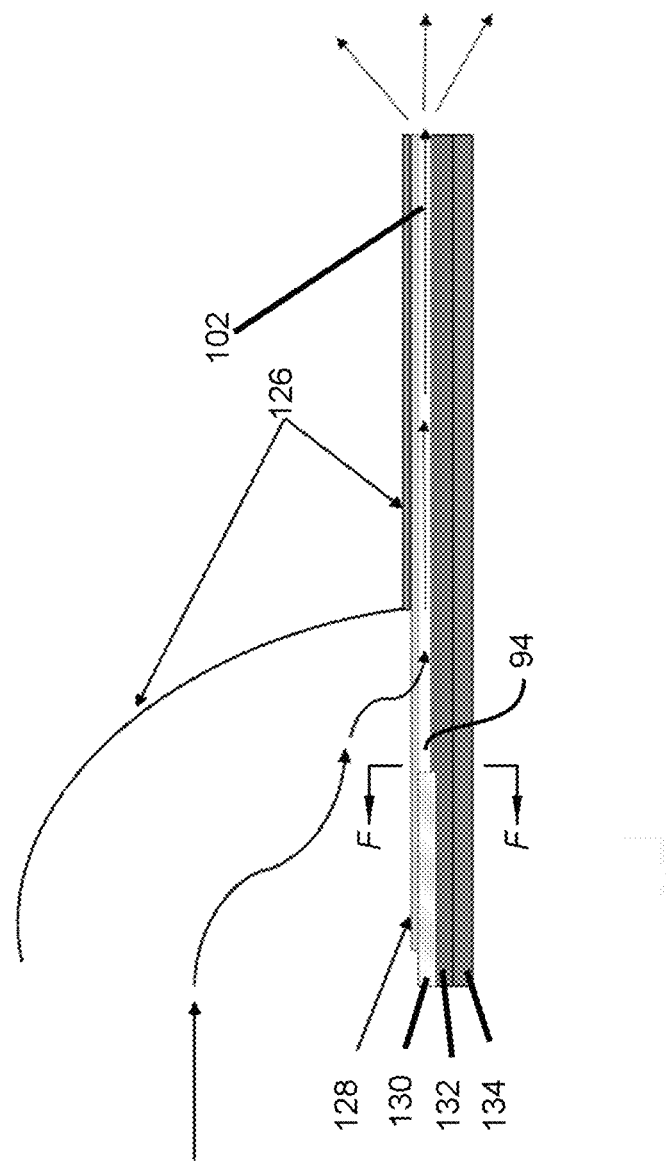
FIG. 17 is a cross-sectional view of a portion of a balloon catheter with a permeable membrane according to one embodiment of the present invention.
Figure 18:
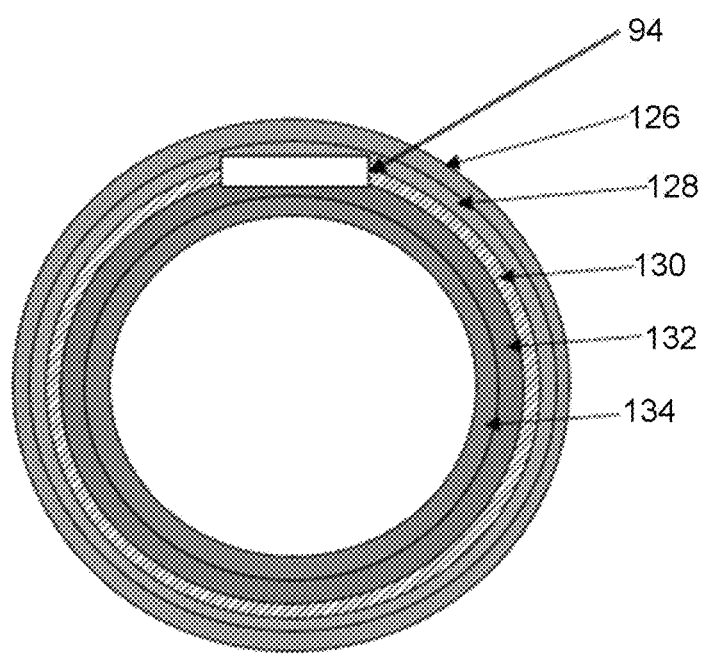
FIG. 18 is a cross-sectional view along line F of FIG. 17 of a balloon catheter with a permeable membrane according to one embodiment of the present invention.

FIGS. 17 and 18 show another embodiment of a purging system used in a balloon catheter according to one embodiments of the present invention that utilizes a membrane which allows passage of air/gas from the balloon while not allowing passage of liquid. The inflation lumen is used to initially inject a liquid inflation media (e.g. contrast agent) to purge residual gas from the balloon and from the balloon catheter before placing the balloon within the patient's body. The catheter includes the purge port 94 which includes a permeable membrane 128 that allows passage of gas but not liquid from the balloon—allowing air to escape while retaining the liquid inflation media. The purge port is linked to a de-airing channel 102 which is in communication with an area external to the balloon 18, such that the air is conveyed from the purge port 94 through the de-airing channel 102 and externally purged from the catheter (shown by arrows). Since the membrane 128 blocks liquid from escaping, the balloon 18 resists leaking so that it can maintain its proper inflated shape of the balloon 18 once the balloon 18 is inflated within the patient's vasculature system.

FIG. 17 shows a distal section of a balloon catheter which includes a balloon 126 and a purging system. The purging system utilizes the purge port 94 which includes a membrane 128, and the de-airing channel 102 linked to the purge port 94. The balloon 126 is proximally bonded to the inflation lumen so that inflation media (e.g. contrast agent) delivered through the inflation lumen inflates the balloon 126. The balloon 126 is distally bonded to the distal portion 30 of the inner assembly/guidewire lumen 16—similar to the configuration shown in FIG. 2. The permeable membrane 128 is placed under the balloon 126. the membrane 128 contains pores which are sized to allow the passage of air/gasses but not liquid.

In one example, the membrane 128 is an ePTFE layer with a thickness of about 0.0006"-0.0007" and a pore size of about 0.4-0.6 microns. The polymer can be treated in a number of different ways to impart pores of an appropriate size to create the membrane. In one preferred embodiment, the polymer is heat treated in order to make the polymer stretchable, the polymer is then stretched to create various pores therein, then reheated to lock in the particular stretched shape. In another embodiment, a chemical is utilized and the chemical eats through the polymer in order to create the membrane. In another embodiment, an e-spun process can be used to create a spider-web like structure with appropriately-sized pores. In another embodiment, the membrane is a porous foam material.

As shown in FIGS. 17 and 18, a ringed radiopaque (e.g. platinum) marker band 130 is placed under only a proximal portion of the membrane 128, a layer 132, for example a polymer layer, sits under the marker band 130, and a liner 134, for example a PTFE liner, sits under the polymer layer 132. The portion of the membrane 128 without the marker band 130 reinforcement-layer defines the purge port 94, while the de-airing channel 102 sits under the more distal portion of the membrane 128 and provides a communication path for the air to an exterior of the distal end of the balloon catheter. The membrane 128 separates balloon 126 and the de-airing channel 102 and helps define the proximal purge-port 94 which acts as an intermediary allowing passage of gas/air but not the passage of liquid, for example the balloon inflation liquid as discussed earlier. The de-airing channel 102 communicates proximally with purge port 94 and distally with an area external of the balloon, so air passing through the membrane 128 of the purge port 94 is conveyed through the de-airing channel 102 and displaced externally, as indicated by the flow arrows shown in FIG. 17. Since the balloon 126 connects to the inner assembly/guidewire lumen, these elements all comprise the distal part of the inner assembly/guidewire lumen. FIG. 18 is a cross sectional view along line F shown in FIG. 17 of the distal part of the inner assembly/guidewire lumen showing how all the layers sit relative to each other, when the balloon 126 is in a deflated state. The layer 134 forms the inner base liner of the guidewire lumen and the balloon 126 forms a top exterior layer of the distal portion of the balloon catheter, a distal most portion of balloon 126 being non-inflatable.

In order to create the purge port 94 and the de-airing channel 102, in one embodiment of the present invention, a 0.001"-0.005" thick mandrel is placed within the polymeric layer 132. The mandrel is then removed leaving a gapped section. The membrane 128 is placed over the gap; the membrane 128, as discussed earlier, has a specific permeability to allow gas molecules but not allow liquids through, therefore the liquid will be retained in the balloon while the gasses escape. The membrane 128 sits over a proximal section of the de-airing channel 102 defining the purge port 94. Gas passes through the purge port 94, through the de-airing channel 102, and out of the distal end of the balloon catheter.

The function of the purge port 94 and membrane 128 in the embodiment shown in FIGS. 17 and 18 is to provide a selective escape path for air but not liquid so that air can escape the balloon 126. The air is then expelled from the balloon 126 via the purge port 94, through the de-airing channel 102 and then out of the distal end of the balloon catheter. To this end, the purge port 94 includes a membrane layer 128 to selectively allow the passage of air but not liquid. As shown in FIG. 17, the membrane 128 spans the entire distal section of the balloon catheter, however the distal part of the balloon 126 is directly bonded to the membrane 128. Since the membrane 128 is directly bonded to the balloon 126, this part of the balloon 126 cannot inflate or deflate. Therefore, the air will only pass out of the balloon 126 through the purge port 94, which is located next to a non-bonded section of the balloon (e.g. a section of the balloon 126 which inflates and deflates).

The method for prepping and using the balloon involves injecting a liquid, such as contrast agent, through the inflation lumen of the balloon catheter to flush out any residual air/gas in the balloon 126. The gas permeates through the purge port 94 and exits the de-airing channel 102 out the distal tip or end of the balloon catheter. The liquid is retained in the balloon, and the user employs aspiration or suction to withdraw the liquid back through the inflation lumen to deflate the balloon 126. Once the balloon catheter is prepped and the residual gases are purged, the balloon catheter is placed into the vasculature and inflated by, again, injecting liquid through the inflation lumen. The balloon 126 will remain inflated since the membrane 128 ensures liquid cannot escape out of the balloon through the purge port 94 and de-airing channel 102.

The embodiments shown and described in FIGS. 17 and 18 can be used with other purge system embodiments shown and described in other figures and in other parts of this application. For instance, FIGS. 13 and 14 utilized a bump 118 to prevent over-aspiration of the balloon. The bump 118 can also be utilized by placing the bump 118 over a portion of the membrane 128, or by placing the bump 118 at a more proximal location, proximal of the membrane 128 to prevent over-aspiration of the balloon.

Figure 19A:
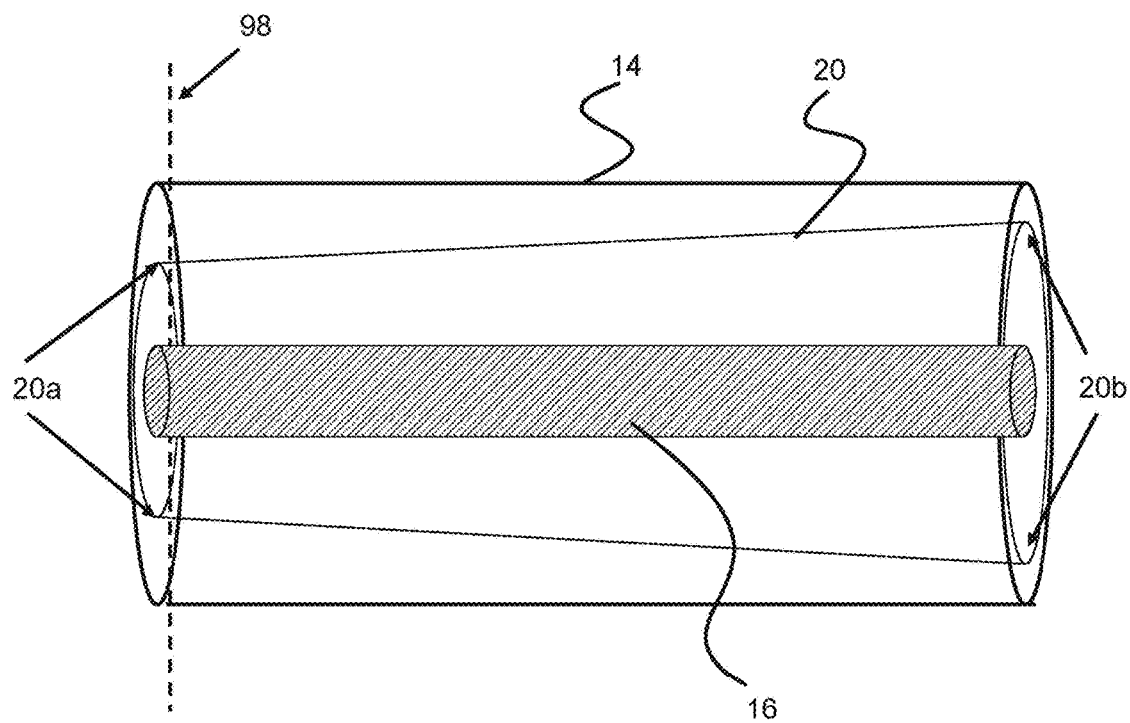
FIG. 19a is a longitudinal view of a portion of a linearly tapered outer lumen of a balloon catheter according to one embodiment of the present invention.

In another embodiment, a diameter of the lumen 20 of the outer assembly 14 is tapered from the proximal to the distal end of the catheter, as shown in FIG. 19a. This taper will result in a tapered inflation lumen. Position 98 indicated by the dashed line shown in FIG. 19a is similar to the distal end of the outer assembly indicated by position 98 in FIG. 2. Inner assembly 16 employs the guidewire lumen of the earlier figures. In one example, the lumen diameter 20a at position 98 is in the range of 0.02"-0.03", and a more specific example is 0.0293". In one example, the lumen diameter 20b at the most proximal position of the balloon catheter is in the range of 0.03"-0.035", a more specific example is 0.0305".

The tapered lumen 20 can be produced by utilizing a tapered mandrel to form the outer assembly 14. The tapered mandrel would result in a tapered inner diameter/lumen 20. The use of a taper means the proximal portion of the balloon catheter has a thinner structural layer and larger inflation volume than the more distal portion of the balloon catheter, which has a thicker structural layer and smaller inflation area. This difference in inflation volume is particularly beneficial for deflation of the balloon, where the higher proximal volume allows for greater suction pressure than would be otherwise possible with a consistent volumetric profile throughout lumen 20.

Figure 19B:
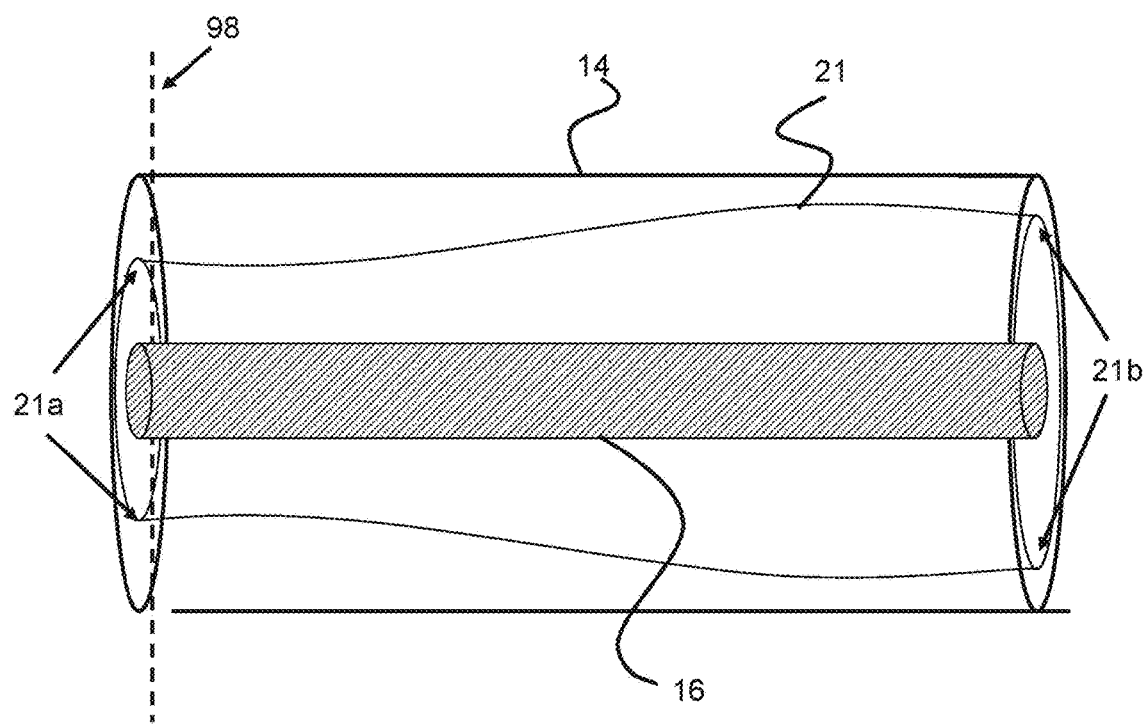
FIG. 19b is a longitudinal view of a portion of a non-linearly tapered outer lumen of a balloon catheter according to one embodiment of the present invention.

FIG. 19b illustrates another example of a tapered inflation lumen 21. Unlike the example in FIG. 19a, the inflation lumen 21 utilizes a non-linear taper that is curved from a larger diameter region 21b to a smaller diameter region 21a. Other shapes are also possible. Preferably, the tapered shape lacks sharp edges to prevent any areas where air can get caught and create eddies or turbulence which would negatively affect the deflation time. The inflation lumen shape can be formed by utilizing a shaped mandrel, and thus various shapes are contemplated by utilizing an appropriately shaped mandrel.

Similar to the earlier embodiments described, the tapered inner lumen 21 can comprise a polymer with a higher melt temperature than outer layers of the outer assembly 14. The outer assembly 14 employing the tapered inner lumen 21 can also include a metallic reinforcement layer.

In another embodiment, a tapered inflation lumen is utilized, but the taper is only utilized on a small portion of the lumen. Balloons and balloon catheters used in the neurovasculature typically have a relatively small size due to the smaller blood vessels in this region of the body. A taper is desirable in order to augment suction pressure; however, a continual taper is difficult to achieve given the limited volumetric capacity of the inflation lumen given the smaller size of the catheter due to the smaller neurovasculature blood vessels. Thus, a taper may be used in a limited portion of the inflation lumen located near the balloon element. In one example the overall inflation lumen length is 60-70 inches, and the taper exists in about 1-6 inches of the inflation lumen length. In one example, since the taper is limited to a small section of the lumen instead of being distributed throughout the lumen, the transition from the smaller diameter to larger diameter section will be fairly significant.

Figure 19C:
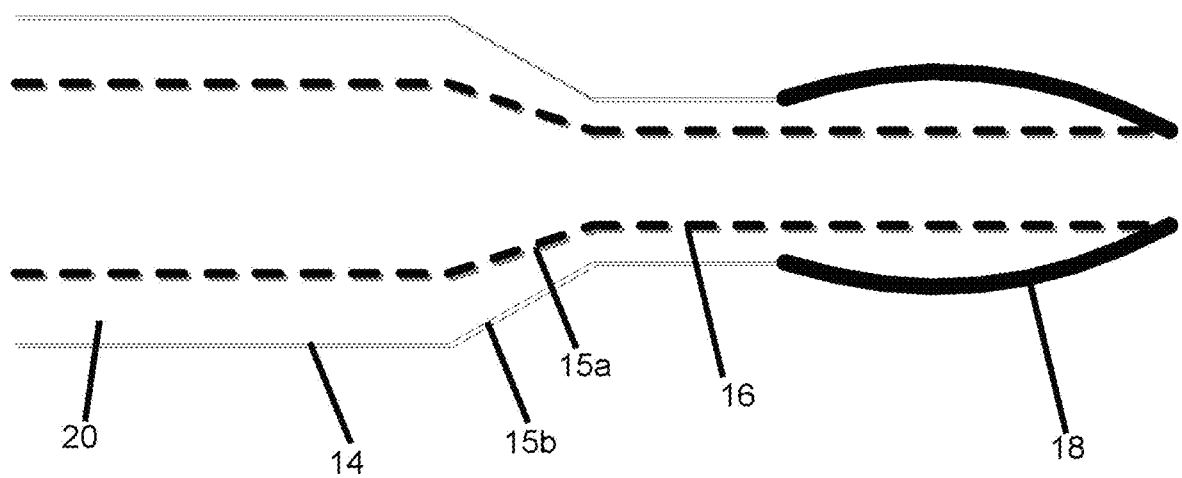
FIG. 19c is a longitudinal view of a portion of a balloon catheter utilizing a localized inner and outer lumen taper according to one embodiment of the present invention.

FIG. 19c shows a localized taper which could be particularly useful in some embodiments. It is generally desirable for a balloon catheter to have a large proximal section and a small distal section, especially in the neurovasculature space. A large proximal section will maximize push force and accommodate a large inflation lumen 20 to speed up inflation and aspiration of the balloon 18. A small distal balloon catheter section allows for a smaller balloon size which is useful to allow placement in the smaller vessels in the neurovasculature—in addition, a smaller distal section will also augment flexibility and navigability of the balloon catheter in the smaller neurovascular blood vessels. FIG. 19c utilizes a relatively consistent larger diameter on the proximal section, a relatively consistent smaller diameter on the distal section of the catheter, and a short taper 15b in between the two sections, this relatively short tapered section allows a quick transition between a large proximal section and a small distal section which includes the balloon 18. This taper can exist and match both on the inner assembly 16 (see inner taper 15a) and outer assembly 14 (see outer taper 15b).

This design also offers some advantages in manufacturing the balloon catheter, since the inner assembly 16 and the outer assembly 14 can be separately manufactured and placed over each other, where one can simply match up the tapers 15a and 15b to ensure the inner assembly 16 and outer assembly 14 are appropriately placed relative to each other, and the inner assembly 16 and the outer assembly 14 can then be bonded together to create the integral balloon catheter. In one example, the section proximal of the taper 15b of the outer assembly 14 has, for example, an outer diameter of about 0.034"-0.038", and the section proximal the taper 15a of the inner assembly 16 has, for example, an inner diameter of about 0.015"-0.020". The section distal of the taper 15b of the outer assembly 14 has, for example, an outer diameter of about 0.020"-0.037", and the section distal the taper 15a of the inner assembly 16 has, for example, an inner diameter of about 0.001"-0.020". The tapered sections 15a and 15b have a length of about 2-3 centimeters, and the section of the balloon catheter distal of the tapered sections 15a and 15b extend distally for about 15-20 centimeters. The section of the balloon catheter proximal of the tapered sections extends for the rest of the length of the catheter, which is about 140 cm.

In another embodiment, both the guidewire lumen 22 and inflation lumen 20 utilize a taper. In one embodiment, the tapers utilized on both lumens extend throughout a substantial length, respectively, on both the guidewire and inflation lumens. In another embodiment, the tapers are present through only a small portion, respectively, of each of the guidewire and inflation lumens (e.g. about 1"-6" of overall length). In one example where both guidewire lumen 22 and inflation lumen 20 utilize a taper, the guidewire lumen 22 has a distal section inner diameter (e.g. distal of the taper) of about 0.01-0.015 inches, and a proximal section diameter (e.g. proximal of the taper) of about 0.015 inches. The inflation lumen 20 has a distal section inner diameter (i.e. distal of the taper) of about 0.023 inches and a proximal section diameter (i.e. proximal to the taper) of about 0.027 inches.

Proper delivery of the appropriate amount of balloon inflation media (e.g. contrast agent) is important, especially in the neurovascular space where smaller balloons are used. Neurovascular balloons are particularly small and can be filled with a small amount of inflation fluid (e.g. 0.01-0.02 milliliters), so it is very easy to under-fill or over-fill a balloon given the limited balloon volume. Normally, a user depresses a syringe to expel inflation fluid from a syringe, but it is difficult to get precise dosing this way. FIGS. 20a-22e show a metered dispensing system utilizing a metered controller to obtain precise and proper metered dispensing of inflation media.

Figure 20A:
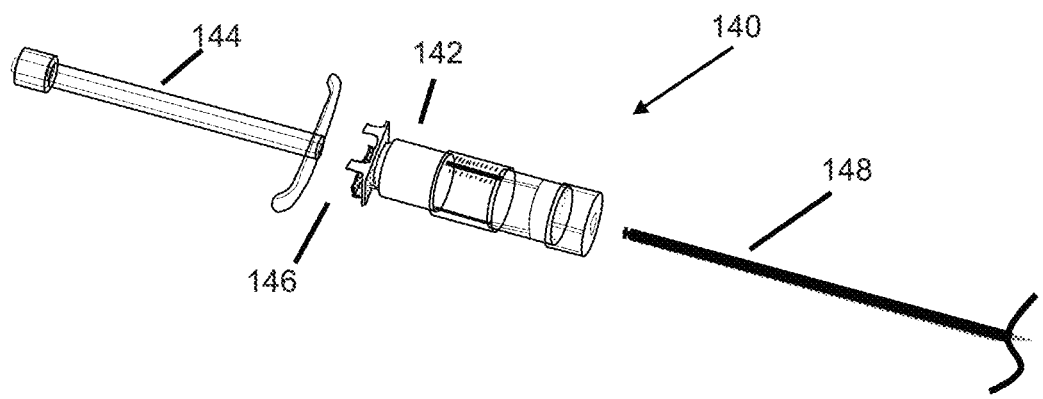
FIG. 20a is an elevation view of a metered dispenser delivery system including a metered controller according to one embodiment of the present invention.

FIGS. 20a-2d illustrate one embodiment of a metered dispensing system which includes a metered controller 140 which can be used with a syringe 144 to deliver precise, metered doses of an inflation fluid (e.g. contrast liquid) from the syringe 144. FIG. 20a shows an expanded view of a dispensing system including a metered controller 140 which can be used on a syringe to provide precise metered dosing. The metered controller 140 includes clip 142 so the controller 142 can affix to a proximal flange 146 of the syringe 144. A plunger 148 passes through a lumen of the metered controller 140 and into the syringe 144. Distal displacement of the plunger 148 will expel fluid from the syringe 144.

Figure 20B:
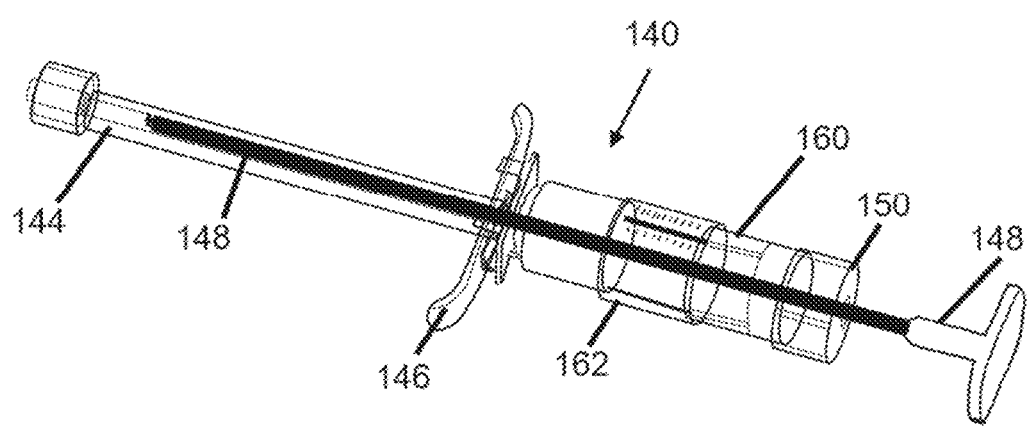
FIG. 20b is an elevation view of the metered dispenser delivery system of FIG. 20a including a metered controller according to one embodiment of the present invention.

FIG. 20b shows the elements of FIG. 20a mated together in an assembled view. The metered controller 140 includes a cap 150 which is in threaded engagement with a top piece 160 of the controller 140 so that the cap 150 can be tightened to the controller 140. The metered controller 140 includes a lumen which accommodates or receives the plunger 148. The clip 142 engages with the syringe proximal flange 146 so that the controller 140 and syringe 144 are connected. A flexible compression piece 158, for example a silicon washer, shown in FIG. 20e, sits around the plunger 150 within the metered controller 140 between the cap 150 and the top piece 160. When the cap 150 is tightened relative to the top piece 160, the cap 150 compresses the compression piece 158 against the top piece 160, and the compression piece 158 engages and locks the plunger 148 thereby preventing free displacement of the plunger 144 relative to the cap 150 and top piece 160. The cap/compression piece/plunger grip mechanism can be thought of as a Tuohy-Borst system.

Figure 20C:
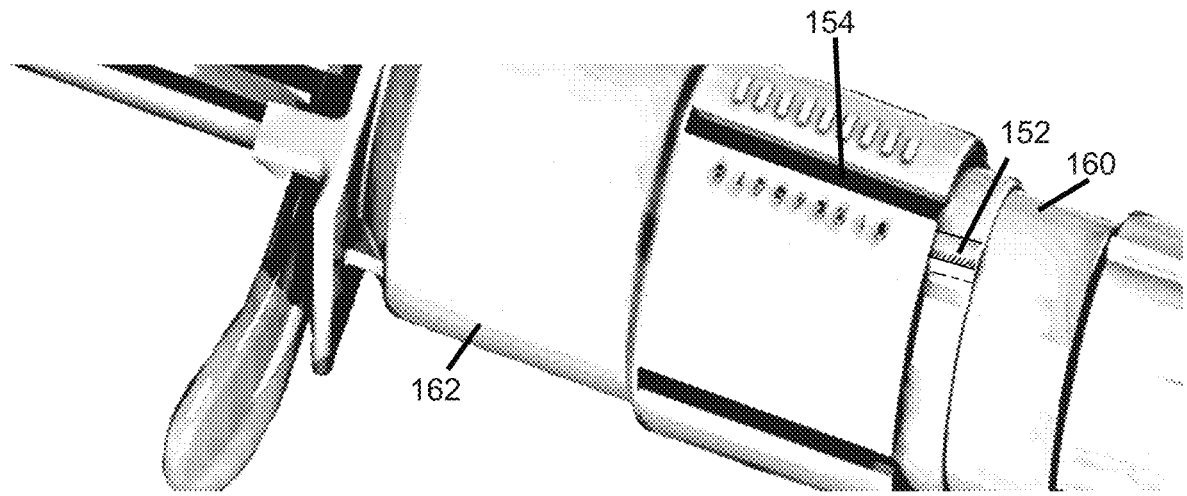
FIG. 20c is a partial elevation view of a metered controller used in the metered dispenser delivery system of FIGS. 20a and 20b according to one embodiment of the present invention, where a protruding element is not aligned with a groove.
Figure 20D:
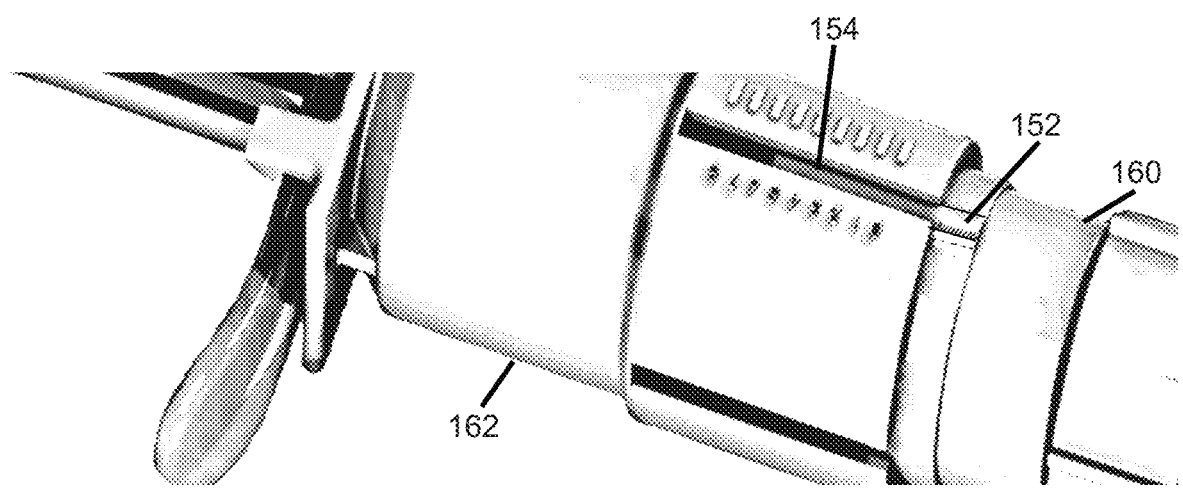
FIG. 20d is a partial elevation view of a metered controller used in the metered dispenser delivery system of FIGS. 20a and 20b according to one embodiment of the present invention, where a protruding element is aligned with a groove.

The metered controller 140 includes a rotational interface to allow metered dispensing. The rotational interface is shown in FIGS. 20c-20d. The controller 140 includes the top piece 160 which includes the cap 150 and a bottom piece 162 that is in threaded engagement with an end of the top piece opposite the cap 150. The top piece 160 is rotatable with respect to the bottom piece 162 and doing so will displace plunger 148 relative to the bottom piece 162 and, hence, relative to the syringe 148. The top piece 160 includes a protruding element 152, and the bottom piece 162 includes a complementary groove 154. There are four grooves 154 around the circumference of the bottom piece 162. The user can rotate the top half of the controller, i.e. the top piece 160 and the cap 150, so that the protruding element 152 is aligned with the groove 154 such that the protruding element 152 sits within the groove 154. When alignment of the protruding element 152 and the groove 154 occurs, a "click" or similar audible feedback will occur. Alternatively stated, the portions of the bottom piece 162 between the grooves 154 may deflect over the rotating protruding element 152 (shown in FIG. 20c) and return to a non-or less deflected state when the protruding element 152 is positioned within the groove 154 (shown in FIG. 20d). Each "click" corresponds to a particular metered dosing, for instance one click can correspond to a precise displacement of the plunger 148 resulting in 0.01 ml or 0.02 ml of inflation fluid being delivered.

For a neurovascular balloon, typically 0.02 ml of inflation fluid (e.g. contrast agent) is sufficient to fill the balloon. Therefore, one click (if each click delivers 0.02 ml) or two clicks (if each click delivers 0.01 ml) will be sufficient to fill the balloon. The controller 140 can further include numbering and a dispensing indicator (for example, a number and a bar next to the number) so the use can tell how much fluid has been delivered. Using the cap 152 and compression piece 158 to lock plunger 148, as discussed above, is important so that the rotation of the controller is then used to displace the plunger in a controlled manner. The metered controller can be designed in different ways, for instance more or fewer grooves 154 can be included to allow more or less dispensing iterations.

Figure 20E:
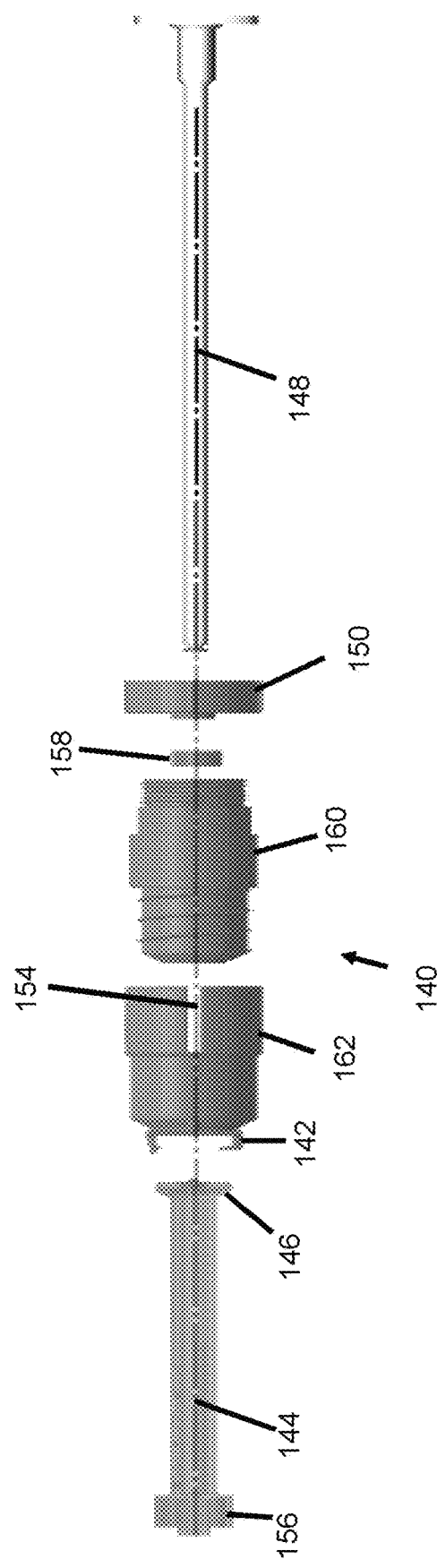
FIG. 20e is an exploded view of the metered dispenser delivery system of FIGS. 20a-20d according to one embodiment of the present invention.

FIG. 20e is an expanded assembly view of the metered controller and metered dispensing system. Syringe 144 includes an interface 156 adapted to mate with a catheter hub to deliver the syringe contents through the catheter. The metered controller 140 includes the bottom piece 162 and the top piece 160. A distal portion of the top piece 160 includes threads so that the top piece 160 and the bottom piece 162 can be engaged with each other and tighten with respect to each other when top piece 160 is rotated by the user. At an opposite, proximal portion of the top piece 160 and the cap 150 are mated together using a threaded engaging mechanism and the compression piece 158 is disposed therebetween and used to lock to plunger 148 in the Touhy-Borst type engagement system described earlier.

Figure 21A:
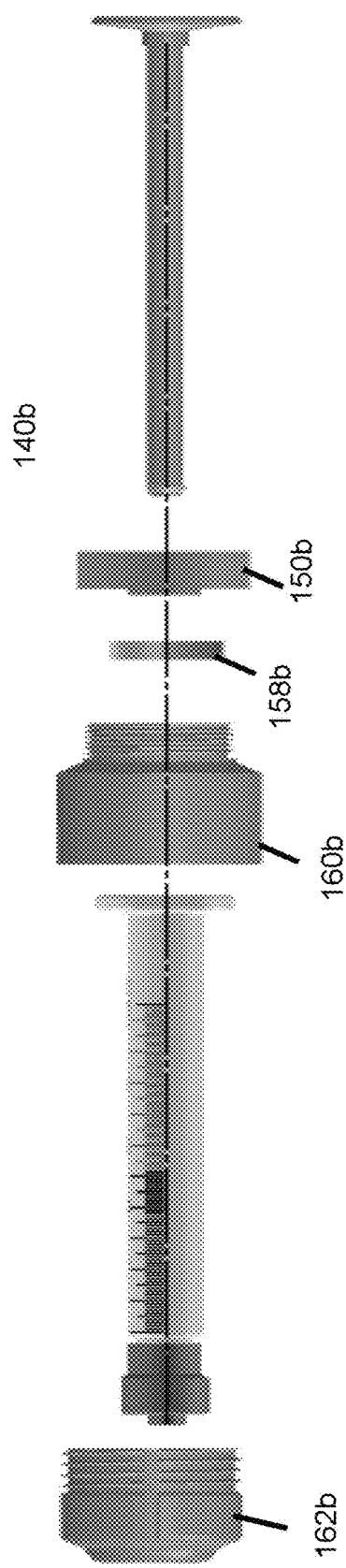
FIG. 21a is an exploded view of a metered dispenser system where a metered controller includes a top piece which sits over a bottom piece according to one embodiment of the present invention.
Figure 21B:
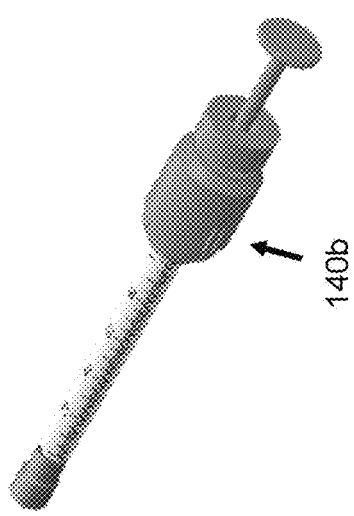

FIGS. 21a and 21b show an alternative embodiment of the metered controller shown in FIGS. 20a and 20e. In this embodiment, a metered controller 140b comprises a top piece 160a and a bottom piece 162b, except here the bottom piece 162b has threads to mate with the top piece 160b such that the top piece mates over the bottom piece. This embodiment would still utilize the audible interface, so the top piece would have a protruding element which contacts a groove on the bottom piece—however unlike the other embodiments, the protruding piece would sit over the groove and thus latch into the groove when the top piece 160a of the controller 140b is rotated by the user relative to the bottom piece 162b. The controller 140b further employs a cap 150b and a compression piece 158b similar to that described relative to the embodiment shown in FIGS. 20a-20e.

Figure 22A:
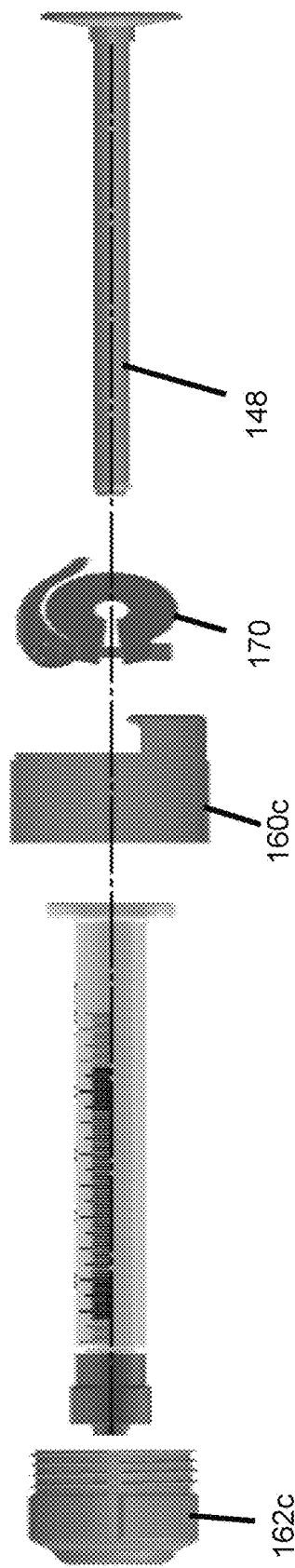
FIG. 22a is an exploded view of a metered dispenser system utilizing a metered controller and a clamp according to one embodiment of the present invention.
Figure 22B:
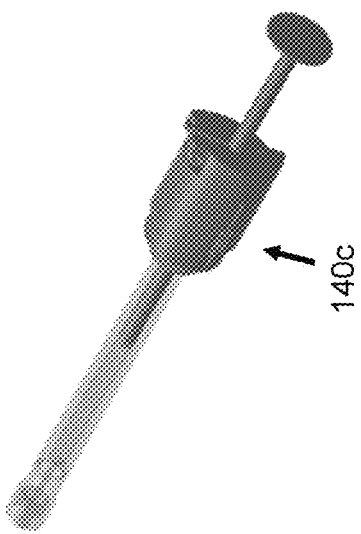

FIGS. 22a and 22b show an alternative embodiment of a metered controller according to the present invention. Like the controller of FIGS. 21a and 21b, a top piece 160c sits over a bottom piece 162c where the bottom piece has threads to accommodate the top piece. Whereas the previous embodiments utilized a cap which is tightened to lock a compression piece to the plunger, here a clamp 170 is used and the clamp 170 tightens such that it is locked with respect to the plunger 148. The top piece 160c of metered controller 140c includes a recess which accommodates the clamp 170. Rotating the top half of the controller will rotate the plunger since the clamp, which is housed by the top piece, is locked to the syringe. The top piece 160c has a protruding piece which mates with a corresponding groove on the bottom piece to produce an audible click at selected intervals, like in the previous embodiments.

In another alternative embodiment, the system of FIGS. 20a-20e, which utilizes a top piece 160 received by a bottom piece 158, could utilize a clamp 170 instead of the compression piece to lock to the syringe plunger. In this embodiment, the top piece would accommodate the clamp, like how the top piece accommodates clamp 170 in FIGS. 22a and 22b.

In one preferred embodiment, the metered controller 140-140c and dispensing system shown in FIGS. 20a and 22b can be used as part of a broader balloon catheter purging and delivery system, used with the purge port/membrane concepts of any of the embodiments described above, for example with the embodiments of FIGS. 17 and 18. The membrane, as discussed earlier, selectively allows passage of gas but not liquid to purge gas from a balloon. The metered controller/metered dispensing system of FIGS. 20a-22b will allow controlled dispensing of a precise amount of inflation fluid (e.g. contrast agent). Since the membrane prevents passage of liquid, the inflation fluid will be retained within the balloon ensuring the balloon can maintain its proper inflated shape after the balloon is inflated.

It is contemplated that any of the embodiments herein described may be employed individually or in combination with any other embodiments herein described.

It is noted that while the present invention has been described with respect to neurological procedures, it is contemplated that certain features of the present balloon catheter also address needs in non-neurological fields.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A balloon catheter for treatment of a patient, comprising:
    a catheter body having an elongated shape, a distal portion, and a proximal portion;
    an inflation lumen located within the catheter body and having a first opening at the proximal portion of the catheter body and a second opening at the distal portion of the catheter body;
    an elongated channel extending along the distal portion of the catheter body;

a membrane disposed over at least a proximal section of the elongated channel, the membrane having pores sized to allow passage of gas while restricting passage of an inflation liquid; and, a balloon having an inflatable portion positioned over the membrane and the proximal section of the elongated channel, and the balloon having an uninflatable portion attached to the distal portion of the catheter body and over a distal section of the elongated channel; and, wherein the uninflatable portion of the balloon is attached to a portion of the membrane" after "channel".

2. The balloon catheter of claim 1, wherein a distal portion of the membrane is positioned between the catheter body and the uninflatable portion of the balloon.

3. The balloon catheter of claim 1, wherein the catheter body further comprises a guidewire lumen.

4. The balloon catheter of claim 1, wherein the balloon catheter further comprises a radiopaque marker band positioned axially between the membrane and the distal portion of the catheter body.

5. The balloon catheter of claim 1, wherein the inflation lumen is coaxial with a guidewire lumen.

6. The balloon catheter of claim 1, wherein the membrane is comprised of an ePTFE layer.

7. The balloon catheter of claim 1, further comprising a purge port linked to the elongated channel.

8. A balloon catheter for treatment of a patient, comprising:
a catheter body having an elongated shape;
an elongated gap extending along a distal portion of the catheter body;
a balloon having a first region that is positioned over and inflatable over a proximal section of the elongated gap, and the balloon having a second region that is attached to the catheter body and over a distal section of the elongated gap; and,
a membrane positioned over the proximal section of the elongated gap and under the first region of the balloon such that the membrane allows passage of gas while restricting passage of inflation liquid, wherein a portion of the membrane is located between the second region of the balloon and the catheter body" after "inflation liquid".

9. The balloon catheter of claim 8, further comprising an inflation lumen positioned in the catheter body and opening underneath the first region of the balloon.

10. The balloon catheter of claim 8, wherein the membrane has pores sized to allow passage of gas while restricting passage of the inflation liquid.

11. The balloon catheter of claim 8, wherein the membrane is further located between the second region of the balloon and a distal section of the elongated gap.

12. The balloon catheter of claim 8, further comprising a guidewire lumen located within the catheter body.

13. The balloon catheter of claim 8, further comprising a syringe and a metered controller that actuates a syringe plunger to expel a metered dose of the inflation liquid from the syringe.

14. The balloon catheter of claim 8, wherein the catheter body comprises an inner assembly and an outer assembly, and wherein the balloon is connected to the inner assembly and the outer assembly.

15. The balloon catheter of claim 8, further comprising an inflation lumen in the catheter body that is tapered so as to decrease in diameter toward the distal portion of the catheter body.

16. The balloon catheter of claim 8, wherein the balloon catheter further comprises a radiopaque marker band positioned axially between the membrane and the distal portion of the catheter body.

17. The balloon catheter of claim 16, further comprising a polymer layer positioned under the radiopaque marker band and a liner positioned under the polymer layer.

18. A balloon catheter for treatment of a patient, comprising:
a catheter body having an elongated shape;
a de-airing means for purging gas extending along a distal portion of the catheter body;
an inflation means having a first region that is positioned over and inflatable over a proximal section of the de-airing means, and the inflation means having a second region that is bonded to the catheter body and over a distal section of the de-airing means; and,
a membrane means for allowing passage of gas while restricting passage of inflation liquid, the membrane means being positioned over the proximal section of the de-airing means and under the first region of the inflation means, wherein the second region of the inflation means is bonded over a distal length of the membrane means.

\* \* \* \* \*